United States Patent [19]

Barton

[11] Patent Number: 5,112,974
[45] Date of Patent: May 12, 1992

[54] MIXED LIGAND COMPLEXES AND USES THEREOF AS BINDING AGENTS TO DNA

[75] Inventor: Jacqueline K. Barton, New York, N.Y.

[73] Assignee: The Trustees of Columbia University in the City of New York, New York, N.Y.

[21] Appl. No.: 268,247

[22] Filed: Nov. 7, 1988

Related U.S. Application Data

[63] Continuation-in-part of Ser. No. 905,295, Sep. 8, 1986, which is a continuation-in-part of Ser. No. 693,023, Jan. 18, 1985, Pat. No. 4,721,669.

[51] Int. Cl.⁵ .................... C07F 15/00; C07D 471.04; A61K 33/24; A61K 31/555
[52] U.S. Cl. .......................... 546/4; 546/10; 546/88; 546/275; 556/136; 556/138; 424/9; 424/11; 424/617; 424/641; 424/646; 424/652; 935/77; 935/88; 204/157.72
[58] Field of Search .......... 546/81, 84, 88, 4, 10, 546/275; 534/15; 556/136, 138; 424/9, 11, 641, 617, 646, 652; 935/77, 78; 204/157.22

[56] References Cited

U.S. PATENT DOCUMENTS

| | | | |
|---|---|---|---|
| 4,699,978 | 10/1987 | Barton | 536/27 |
| 4,721,669 | 1/1988 | Barton | 435/6 |
| 4,980,473 | 12/1990 | Barton | 546/10 |

OTHER PUBLICATIONS

Schlosser et al., Chem. Abst. 76-67526p (1972).
Schlosser et al., Chem. Abst. 76-119340v (1972).
Schlosser et al., Chem. Abst. 82-37043k (1975).
Pyle et al., Chem. Abst. 107-189571d (1987).
Belser et al., Inorg. Chem. 1981; 20:3098-3103.
Barton, K. K., J. Biomol. Struct. Dyn. 1983; 1:621-632.
Ackerman, M. N. and Interrante, L. V., Inorg. Chem. 1984; 23:3904-3911.
Barton, J. K. and Raphael, A. L., Proc. Natl. Acad. Sci. USA 1985; 82:6460-6464.

Barton, J. K. and Lolis, E., J. Am. Chem. Soc. 1985; 107:708-709.
Barton, J. K. et al., J. Am. Chem. Soc. 1986; 108:2081-2088.
Barton, J. K., Science 1986; 233:727-734.
Goldstein, B. M. et al., Inorg. Chem. 1986; 25:842-847.
Kumar, C. V. et al., Inorg. Chem. 1987; 26:1455-1457.
Pyle, A. M. and Barton, J. K., Inorg. Chem. 1987; 26:3820-3823.
Kirshenbaum, M. R. et al., Nucleic Acids Research 1988; 16:7943-7960.
Mei, H-Y and Barton, J. K., Proc. Natl. Acad. Sci. USA 1988; 85:1339-1343.
Baum, R. M., C&EN, pp. 22-25, Jun. 12, 1989.

Primary Examiner—Cecilia Shen
Attorney, Agent, or Firm—John P. White

[57] ABSTRACT

This invention concerns a coordination complex or salt thereof which is spectroscopically or photoactively determinable when bound to DNA having the formula

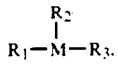

wherein M is a suitable transition metal and each of $R_1$, $R_2$ and $R_3$ is ethylenediamine, bipyridine, phenanthroline, diazafluorene-9-one or phenanthrenequinonediimine. In the complex, $R_1$, $R_2$ and $R_3$ are bound to M by coordination bonds and $R_1$ and $R_2$ may be the same or different and both are different from $R_3$. In the preferred embodiments, the invention concerns complexes of ruthenium(Ru) or rhodium(Rh) wherein $R_1$ and $R_2$ are the same. The invention also concerns the complex

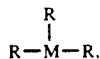

wherein M is Ru or Rh and R is 9-10-phenanthrenequinonediimine or 5-nitrophenanthroline.

25 Claims, 28 Drawing Sheets

Ru(phi)$_3^{2+}$

Δ Ru(DIP)$_2$(phen)$^{2+}$

Δ Ru (phen)$_3^{2+}$

Δ Ru(phen)₂(phi)²⁺

1,10-phenanthroline
(phen)

2,2'-bipyridyl
(bpy)

9,10-phenanthrene-
quinonediimine
(phi)

4,7-diphenylphenanthroline
(DIP)

5-nitrophenanthroline
(5-NO₂-phen)

4,5-diazafluorene-9-one
(flone)

Figure 8A₁
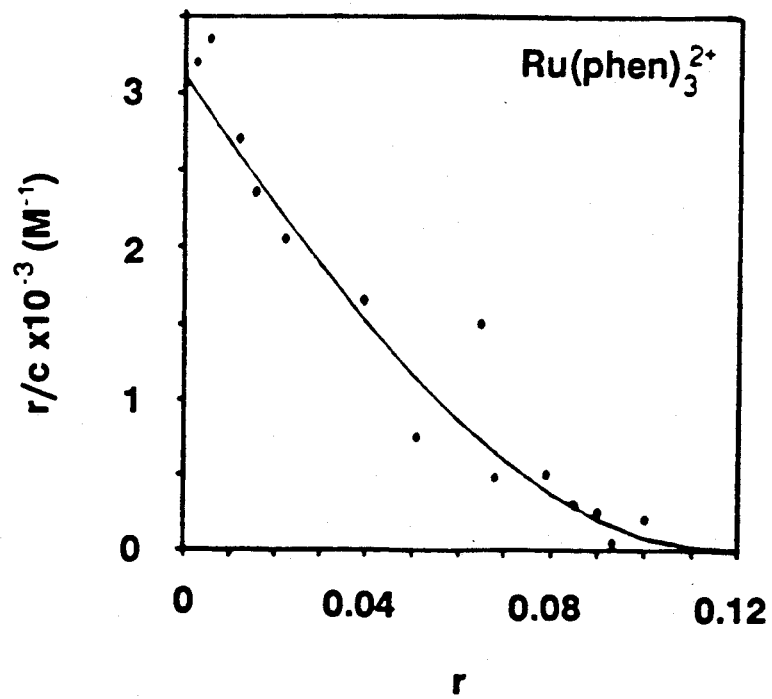

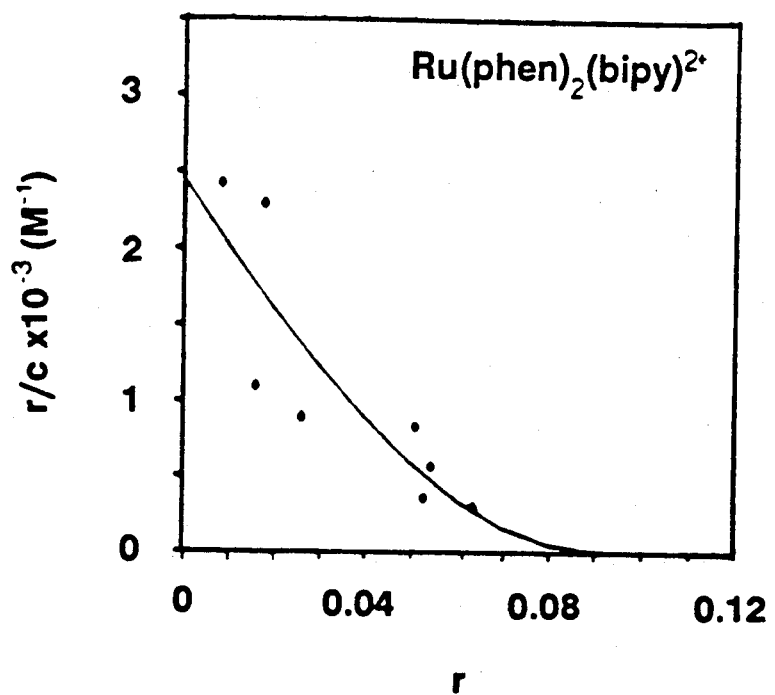
Figure 8A₂

Figure 8A₃
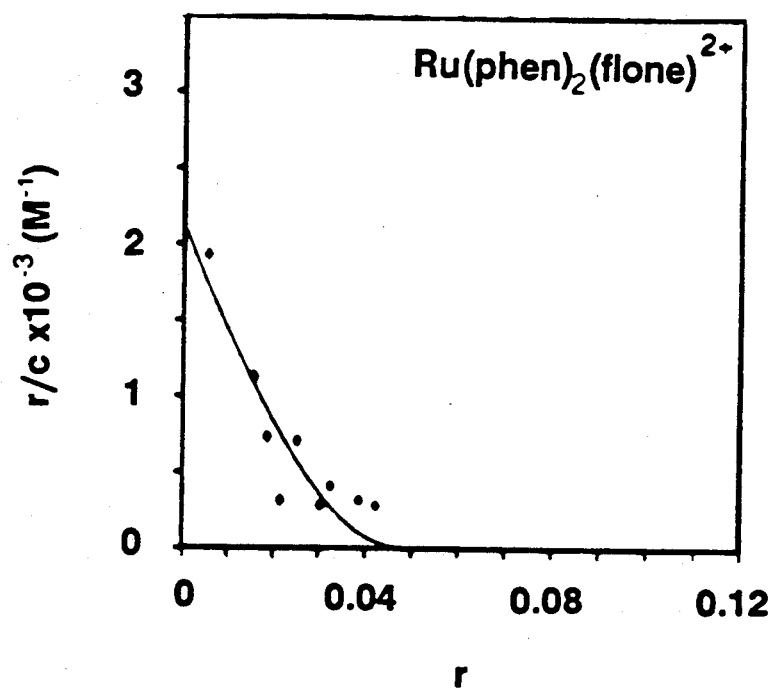

Figure 8A$_4$
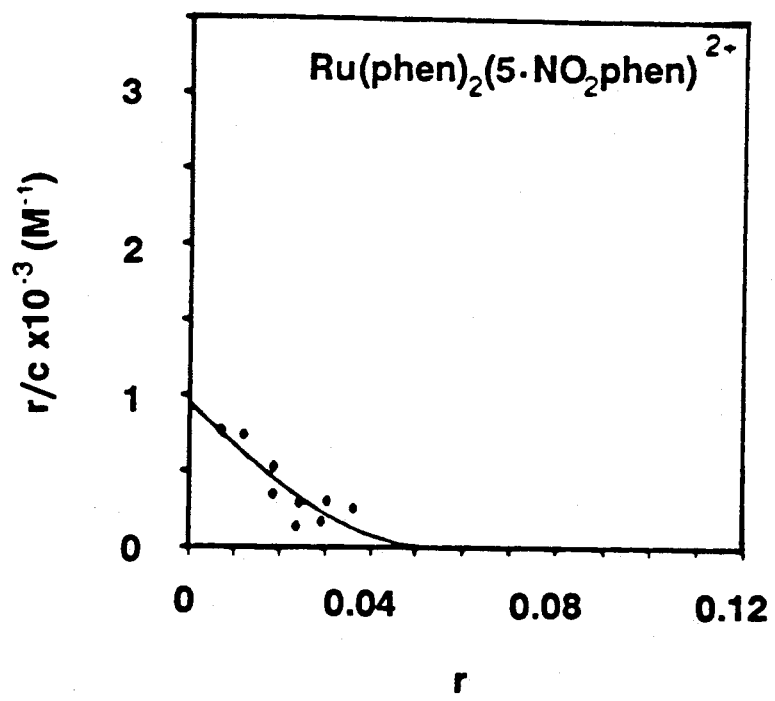

Figure 8A$_5$
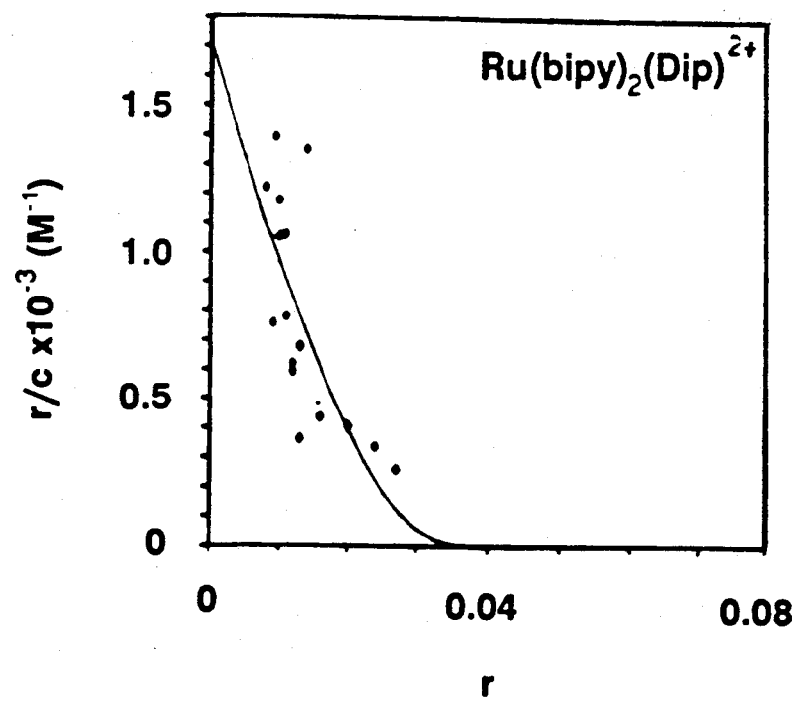

Figure 8A$_6$
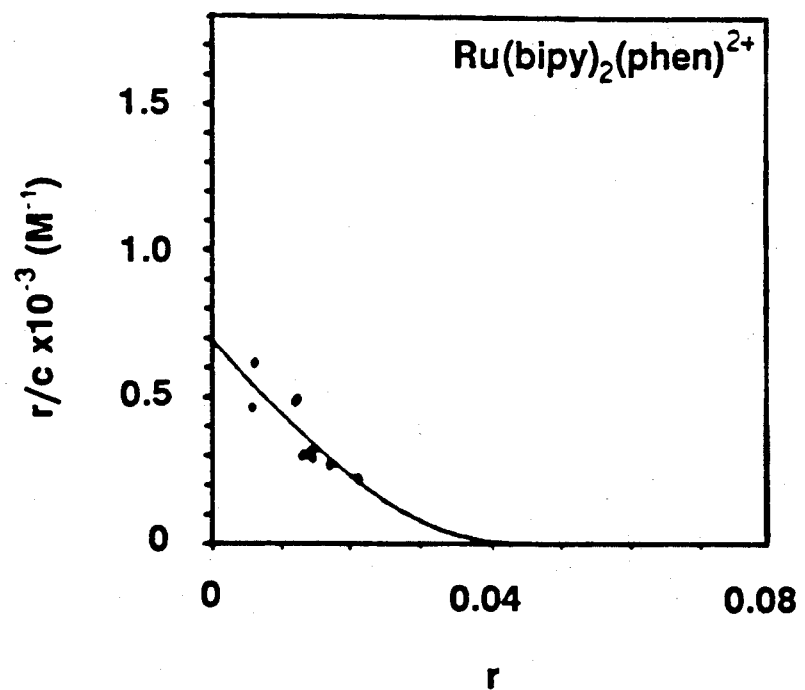

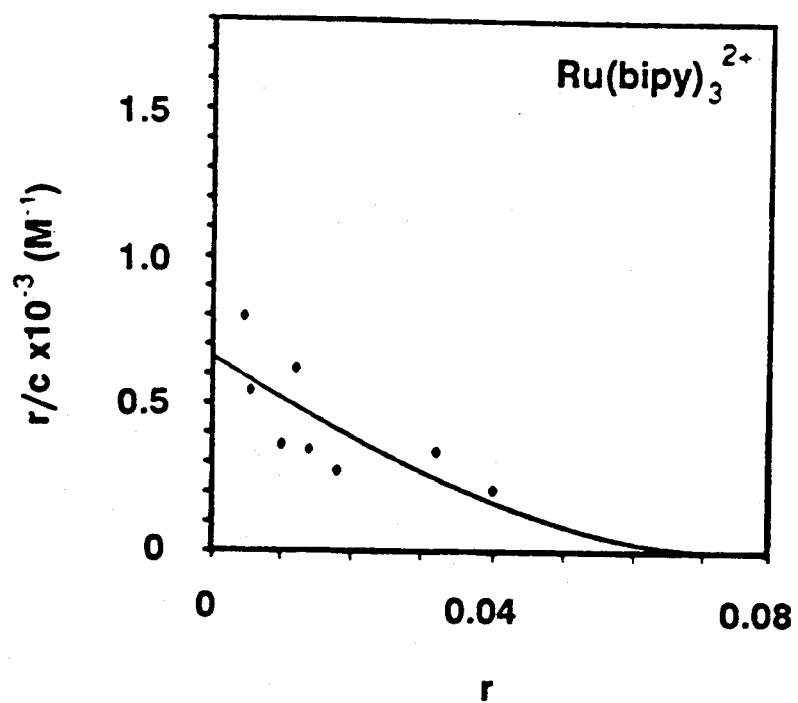
Figure 8A$_7$

MIXED LIGAND COMPLEXES AND USES THEREOF AS BINDING AGENTS TO DNA

The invention was made with government support under grant number GM 33309 from the National Institutes of Health of the U.S. Department of Health and Human Services and with the support of the National Science Foundation and the Army Office of Research.

This application is a continuation-in-part of U.S. Ser. No. 905,295, filed Sep. 8, 1986, which in turn is a continuation-in-part of U.S. Ser. No. 693,023, filed Jan. 18, 1985, now U.S. Pat. No. 4,721,669, issued Jan. 26, 1988, the contents of which are hereby incorporated by reference into the present application.

BACKGROUND OF THE INVENTION

Some of the information set forth herein has been published. See Pyle. A. M. and Barton. J. K., Mixed Ligand Complexes and Uses Thereof as Binding Agents to DNA, Inorganic Chemistry, 1987, 26:3820–3823, which was distributed by the publisher on Nov. 6, 1987.

Throughout this application various publications are referenced by arabic numerals within parentheses. Full citations for these publications may be found at the end of the specification immediately preceding the claims. The disclosures of these publications in their entireties are hereby incorporated by reference into this application in order to more fully describe the state of the art to which this invention pertains.

There has been considerable interest in elucidating those factors which determine affinity and selectivity in binding of small molecules to DNA. (22–28) A quantitative understanding of such factors which determine recognition of DNA sites would be valuable in the rational design of sequence-specific DNA binding molecules for application in chemotherapy and in the development of tools for biotechnology. Much work has focused on the elucidation of non-covalent interactions with DNA by small natural products and their synthetic derivatives. (23–28) These small molecules are stabilized in binding to DNA through a series of weak interactions, such as the $\pi$-stacking interactions associatied with intercalation of aromatic heterocyclic groups between the base pairs, and hydrogen bonding and Van der Waals interactions of functionalities bound along the groove of the DNA helix. It would be valuable to understand quantitively the contributions from these different modes to stabilization of the bound complex at a DNA site.

Previous work has focused on the examination of non-covalent interactions with DNA of transition metal complexes of phenanthroline (22, 29–32) The cationic complexes has been found both to intercalate into DNA and to bind non-covalently in a surface-bound or gove-bound fashion. These interactions with DNA have been characterized largely through spectroscopic and photophsical studies, and determinations of enantiomeric selectivities associated with binding by the metal complexes have been helpful also in establishing models. (29, 30) On the basis of these investigations, intercalation likely occurs preferentially from the major groove of the DNA helix and is favored for the isomer into a right-handed helix. In the case of the surface-bound interaction, it likely occurs along the minor groove of the helix and it is the Λ isomer which is favored in surface-binding to right-handed DNA helices. FIG. 5 illustrates models for these binding interactions.

Based upon these binding interactions, derivatives of tris (phenanthroline) complexes have been developed which recognize selectively different conformations of DNA. By matching shapes and symmetries of the metal complexes to those of DNA conformations, probes for A- and Z-DNA have been designed. (31) Most recently, a diphenylphenanthroline complex of rhodium (III) has been found to induce double-stranded cleavage at cruciform sites upon photoactivation. (32) Although these complexes lack hydrogen bonding donors and acceptors and therfore must be associating with the DNA only through a mixture of Van der Waals and intercalactive interactions, a high level of specificity is associated with the recognition of different DNA sites by these complexes.

The present invention involves mixed ligand complexes and complexes having three phenanthrenequinone diiamine ligands. The mixed ligand complexes of ruthenium (II) were explored for their interactions with B-DNA using a variety of biophysical and spectroscopic methods. Mixed ligand complexes of phenanthroline, phenanthrenequinonediimine, and derivatives thereof have been found to be useful for the construction and characterization of DNA-binding molecules. The ruthenium (II) complexes are particularly useful owing to their intense optical absorption and emission, their relative ease of preparation, and their inertness to substitution and racemization. (33–35)

SUMMARY OF THE INVENTION

This invention concerns a coordination complex or salt thereof which is spectroscopically or photoactively determinable when bound to DNA having the formula

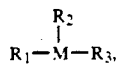

wherein M is a suitable transition metal and each of $R_1$, $R_2$ and $R_3$ is ethylenediamine, bipyridine, phenanthroline, diazafluorene-9-one or phenanthrenequinonediimine. In the complex, $R_1$, $R_2$ and $R_3$ are bound to M by coordination bonds and $R_1$ and $R_2$ may be the same or different and both are different from $R_3$. In the preferred embodiments, the invention concerns complexes of ruthenium(Ru) or rhodium(Rh) wherein $R_1$ and $R_2$ are the same. The invention also concerns the complex

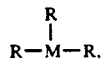

wherein M is Ru or Rh and R is 9-10-phenanthrenequinonediimine or 5-nitrophenanthroline.

The invention also concerns a method for labeling double stranded DNA with the complex which comprises contacting the DNA with the complex so that it binds to and labels the DNA. In a particular embodiment the complex is used to selectively label a conformation present in the double standed DNA which comprises contacting the DNA with the complex or an isomer of the complex so that the complex or the isomer binds to the conformation. The invention also concerns a method for detecting the presence of the conformation present in double stranded DNA which comprises selectively labeling the conformation and then detecting the presence of the complex or the isomer of the complex bound to the conformation. The invention also concerns a method for nicking double stranded DNA by effecting breakage of at least one phosphodiester bond along the DNA which comprises contacting the DNA with the coordination complex under conditions such that the complex binds to the DNA to form an adduct and irradiating the adduct so formed with visible light or ultraviolet radiation of an appropriate wavelength which is absorbed by the complex so as to nick the DNA at the site of binding. Also provided is a method for cleaving double stranded DNA which comprises nicking the DNA according to the present invention and treating the nick DNA so produce with an enzyme which is not deactivated in the presence of the complex used for nicking DNA and is capable of cleaving single stranded DNA so as to cleave the DNA at the site of the nick.

The invention also provides a method for killing a portion of a population of appropriate tumor cells which comprises contacting the tumor cells under suitable conditions with an effective amount of the coordination complex so as to kill the tumor cells. Lastly, the invention concerns a method for treating a subject afflicted with a virus which comprises administering to the subject an effective antiviral amount of the complex so as to kill the virus or inhibit its growth.

DETAIL DESCRIPTION OF THE INVENTION

Figure 1:
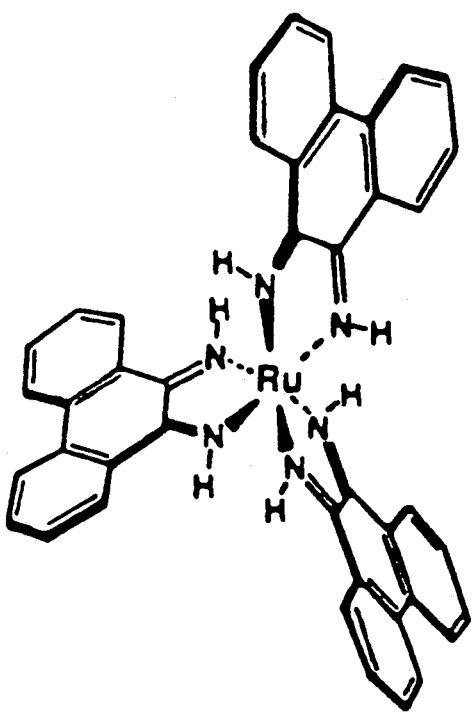
FIG. 1: $Ru(phi)_3^{2+}$.

This invention concerns a coordination complex or salt thereof which is spectroscopically or photoactively determinable when bound to the DNA having the formula

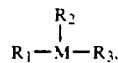

wherein M is a suitable transition metal and each of $R_1$, $R_2$ and $R_3$ is ethylenediamine or a substituted derivative thereof, bipyridine or a substituted derivative thereof, phenanthroline or a substituted derivative thereof, diazafluorene-9-one or a substituted derivative thereof, or phenanthrenequinonediimine or a substituted derivative thereof; wherein $R_1$, $R_2$ and $R_3$ are bound to M by coordination bonds and wherein $R_1$ and $R_2$ are the same or different and both are different from $R_3$. Suitable transition metals include ruthenium(Ru), rhodium(Rh), cobalt(Co), iron(Fe), chromium(Cr), copper(Cu), zinc(Zn), cadmium(Cd), or lead(pb). To date, ruthenium, rhodium and cobalt have proven to be the most effective. Preferred groups for $R_1$, $R_2$ and $R_3$ are 2,2'-bipyridine(bpy), 1,10-phenanthoroline(phen), 4,5-diazafluorene-9-one(flone), 9,10-phenanthrenequinonediimine(phi), 4,7-diamino-1,10-phenanthroline; 3,8-diamino-1,10-phenanthroline; 4,7-diethylenediamine-1,10-phenanthroline; 3,8-diethylenediamine-1,10-phenanthroline; 4,7-dihydroxyl-1,10-phenanthroline; 3,8-dihydroxyl-1,10-phenanthroline; 4,7-dinitro-1,10-phenanthroline; 3,8-dinitro-1,10-phenanthroline; 4,7-diphenyl-1,10-phenanthroline (DIP); 3,8-diphenyl-1,10-phenanthroline; 4,7-dispermine-1,10-phenanthroline; 3,8-dispermine-1,10-phenanthroline; 5-nitrophenanthroline (5-NO$_2$phen); 3,4,7,8-tetramethylphenanthroline (TMP), 4,4' diphenyl bipyridine; bis 4,4' methyl bipyridylate and bis 4,4' bipyridylamide.

In the preferred embodiments of the invention the complex has the formula M(phen)$_2$(phi), M(bpy)$_2$(phi), M(phi)$_2$(bpy), M(phi)$_2$(4,4' diphenyl bipyridine), M(bis 4,4' methyl bipyridylate)$_2$(phi), M(bis 4,4' bipyridylamide)$_2$(phi), M(bpy)$_2$(phen), M(phen)$_2$(bpy), M(phen)$_2$(flone), M(bpy)$_2$(DIP), M(phen)$_2$(DIP), M(ethylenediamine)$_2$(phi), M(phi)$_3$, M(5-NO$_2$phen)$_3$ or M(DIP)$_2$(phen) wherein M is Ru, Rh or Co.

Especially preferred are the following complexes: Ru(bpy)$_2$(phen)$^{2+}$, Ru(phen)$_2$(bpy)$^{2+}$, Ru(phen)$_2$(flone)$^{2+}$, Ru(bpy)$_2$(DIP)$^{2+}$, Ru(phen)$_2$(DIP)$^{2+}$, Ru(DIP)$_2$(phen)$^{2+}$, Ru(phi)$_2$(bpy)$^{2+}$, Ru(phen)$_2$(phi)$^{2+}$, Ru(bpy)$_2$(phi)$^{2+}$, Rh(phi)$_2$(bpy)$^{3+}$, Rh(phen)$_2$(phi)$^{3+}$, Rh(phi)$_2$(4,4' diphenyl bipyridine)$^{3+}$, Rh(bis 4,4' methyl bipyridylate)$_2$(phi)$^{3+}$, Rh(bis 4,4' bipyridylamide)$_2$(phi)$^{3+}$.

Further, the invention concerns the optically resolved delta and lambda isomers of the complex. It has unexpectedly been found that the complex or the delta or lambda isomer of the complex binds add labels DNA. More specifically, the complex or isomer of the complex binds and labels specific conformations of DNA preferentially, i.e. A-DNA, Z-DNA, B-DNA or cruciforms of DNA. The complexes bind to DNA by intercalation or surface binding by means of hydrogen bonding or weak Van der Waals interactions. The method of labeling DNA or specifically labeling a conformation on DNA is effected by contacting the DNA with the complex of the present invention (or an isomer) so that the complex binds to the DNA, preferably at the conformation, thereby labeling the DNA or conformation. The method of labeling may be used to detect the presence of a conformation present in double stranded DNA by selectively labeling the conformation and then detecting the presence of the bound complex or the isomer of the complex. The complex may be detected by spectroscopic methods or photoactive means.

Still another embodiment of this invention is a method for nicking double stranded DNA by effecting single stranded scission, i.e. breakage of at least one phosphodiester bond along the DNA. The method preferably involves contacting the DNA with a cobalt or rhodium containing complex of the invention under suitable conditions such that the complex binds to the DNA so as to form a adduct and irradiating the adduct so form with visible light or ultraviolet radiation of an appropriate wavelength so as to nick the DNA at the site of binding. An appropriate visible or ultraviolet wavelength in this and other embodiments of the invention is a wavelength which is absorbed by the complex used. As described hereinafter, the ligand band absorption of a complex of this invention may be determined spectroscopically by conventional methods. It is also contemplated that the method for nicking DNA may be preformed in vivo.

The invention further involves a method of cleaving double stranded DNA which comprises nicking the DNA by the above-mentioned method and treating the nicked DNA so produced with a suitable enzyme capable of cleaving single stranded DNA under conditions effective to cleave the nicked, double stranded DNA at the site of the nick. By this method double stranded scission of the DNA is effected. Suitable enzymes for effecting double stranded cleavage of nicked DNA in this and other embodiments includes those which are not deactivated in the presence of the complex used for DNA nicking, e.g. S1 nuclease. It is further contemplated that this method for cleaving DNA may also be preformed in vivo. The invention also involves a method for selectively nicking or selectively cleaving DNA at a specific conformation by using the complex or an isomer of the complex such as delta and lambda enantiomer. Appropriate conformations at which the complex may be used to nick or cleave the DNA include Z-DNA, A-DNA, B-DNA or cruciforms of DNA.

It is also contemplated that the complex may be used for labeling, detecting, nicking, or cleaving other forms of double stranded polynucleotides such as double stranded RNA and double stranded DNA-RNA hybrids.

Moreover, the invention provides a method for killing a portion of a population of appropriate tumor cells. The method involves contacting the tumor cells under suitable conditions with an effective amount of the complex or an isomer of the complex to kill the tumor cells. The method may further comprise irradiation the tumor cells with visible light or ultraviolet radiation of an appropriate wavelength at a suitable time after the tumor cells have been contacted with the complex, thereby permitting the complex to nick the DNA of the tumor cells. The method may be used for the treatment of a subject afflicted with tumor cells so as to cause regression of the tumor cells. Administration of the complex to the subject may be parenteral, oral, or topical.

Lastly, the invention concerns a method for treating a subject afflicted with a virus which comprises administering to the subject an effective antiviral amount of the complex so as to kill the virus or inhibit its growth.

EXPERIMENTAL DETAILS

I. Synthesis and Characterization of Ru(phi)$_3^{-2}$ and Zn(phi)$^{-2}$

Ligand Synthesis. 9,10-Phenanthrenequinone bis((trimethylsilyl)-imine) (silylphi) was synthesized from 9,10-phenanthrenequinone (Aldrich) and sodium bis(trimethylsilyl)amide (Fluka) as described by Tuchtenhagen and Ruhlmann. (11) Important modifications to this synthesis include a reaction temperature of no greater than 65° C. and a final phenanthrenequinone concentration of 0.08 M. Under these conditions, orange crystalline silylphi was obtained in 37% yield and stored under nitrogen. The phenanthrenequinone diimine ligand (phi) was generated and chelated in situ by combining the silylated imine ligand with an ethanolic solution of metal chloride by using a modificaiton of Schlosser's method. (12)

[Ru(phi)$_3$]Cl$_2$. A 1.025-g sample of 9,10-phenanthrenequinone bis((trimethylsilyl)imine (2.9 mmol) dissolved in 75 mL benzene was added to a vigorously stirring suspension of Ru(DMSO)$_4$Cl$_2$ (Alfa Products; 0.355 g, 0.73 mmol) in 25 mL of EtOH and 75 mL of benzene. All solvents were dried and distilled under nitrogen before use. This mixture was heated at 65° C. for 1 h until a rich purple solution was generated. The reaction vessel was then opened to the air. After the crude reaction mixture was filtered, it was cooled and evaporated to a small volume. Ru(phi)$_3$Cl$_2$ was precipitated with diethyl ether and collected on a frit.

Solid [Ru(phi)₃]Cl₂ was washed with acetone to remove several blue byproducts (13) and then with diethyl ether to remove organic material resulting from in-air decomposition of excess ligand. After several diethyl ether precipitations from ethanol solutions, Ru(phi)₃]Cl₂ was washed with H₂O to give a final yield of 51%. Samples were often further purified by cellulose column chromatography.

The ¹H NMR spectrum of [Ru(phi)₃]Cl₂ is indicative of a symmetrical, D₃metal chelate with resonances at 7.6 (2 H, tiplet), 8.22 (1 H, doublet), 8.8 (1 H, doublet), and 14.2 ppm (1 H, singlet imine). This is confirmed by elemental analysis Anal. Calcd for Ru(phi)₃Cl₂.H₂O: C, 62.38; H, 3.99; N, 10.39; Ru, 12.90. Found: C, 62.29; H, 4.21; N, 10.0; Ru, 13.10. Fast atom bombardment (FAB) mass spectroscopy of [Ru(phi)₃]Cl₂ showed a strong Ru(phi)₃²⁺ molecular ion of $M_r$ 719 with the next largest peak being the Ru(phi)₂²⁺ fragment at $M_r$ 514. Infrared spectroscopy revealed characteristic imine N—H stretches at 3274 and 3167 cm⁻¹ and a C=N stretch at 1497 cm⁻¹.

Zn(phi)Cl₂. The zinc complex was synthesized as described for [Ru(phi)₃]Cl₂. Yellow Zn(phi)Cl₂ was filtered directly out of the reaction mixture in quantitative yield and washed with diethyl ether, H₂O and acetone. Anal Calcd for Zn(phi)Cl₂·⅓C₆H₆: C, 52.15; H, 3.29; N, 7.60; Cl, 19.23. Found: C, 52.14; H, 3.71; N, 7.21; Cl, 18.50. The molecular ion by FAB was the Zn(phi)Cl⁻ cation of $M_r$ 307 as expected for the proposed structure.

The ¹H NMR of Zn(phi)Cl₂ is slightly complicated by the fact that it dissolves only in coordinating solvents such as DMSO or DMF. Upon dissolution, the tetrahedral structure changes to octahedral as two molecules of solvent bind cisoid to the metal center. The resulting species has several isomers and a $C_1$ symmetry that renders each proton nonequivalent. Although imine protons are epecially affected by the different steric environment of the isomers, there is an integral of two imine protons for each eight aromatic protons. C--H resonances in DMF: 8.52 (1 H, doublet), 8.36 (1 H, doublet), 8.21 (2 H, multiplet), 7.74 (1 H, triplet), 7.55 (2 H, triplet), 7.39 ppm (1 H, mult). N--H resonances: 12.35 (1 H, s), 12.0 (⅓ H, s), 11.8 (⅓ H, s) 11.6 ppm (⅓ H, s).

Instrumentation. Ultraviolet-visible absorption experiments were performed by using a Varian-Cary 219 spectrophotometer and ¹H NMR measurements on a Varian VXR-300 spectrometer. Cyclic voltammetry was conducted by using an IBM voltamograph and recorder. Flash photolysis experiments were made with a YAG laser, monitored with an optical multichannel analyzer interfaced to a PDP 11/23.

Results and Discussion

Synthesis and Characterization. The complex Ru(phi)₃²⁺ can be synthesized from the silylated phi ligand in greater than 51% yield. Alternate synthetic schemes, involving metal reduction and concomitant oxidation of coordinated diaminophenanthrene, were less reproducible and gave poor yield. [Ru(phi)₃]Cl₂ is a stable molecule that does not decompose upon exposure to air or by continuous irradiation with visible light. The ligand is not similarly stable but instead rapidly condenses to the dimeric phenanthroimidazole. Hence spectral comparisons between coordinated ruthenium complexes and free ligand cannot be easily accomplished. The zinc complex was therefore synthesized to provide a spectroscopic analogue for the coordinated ligand. Despite reflux with high ligand concentrations, only the monophi zinc adduct formed.

Figure 2:
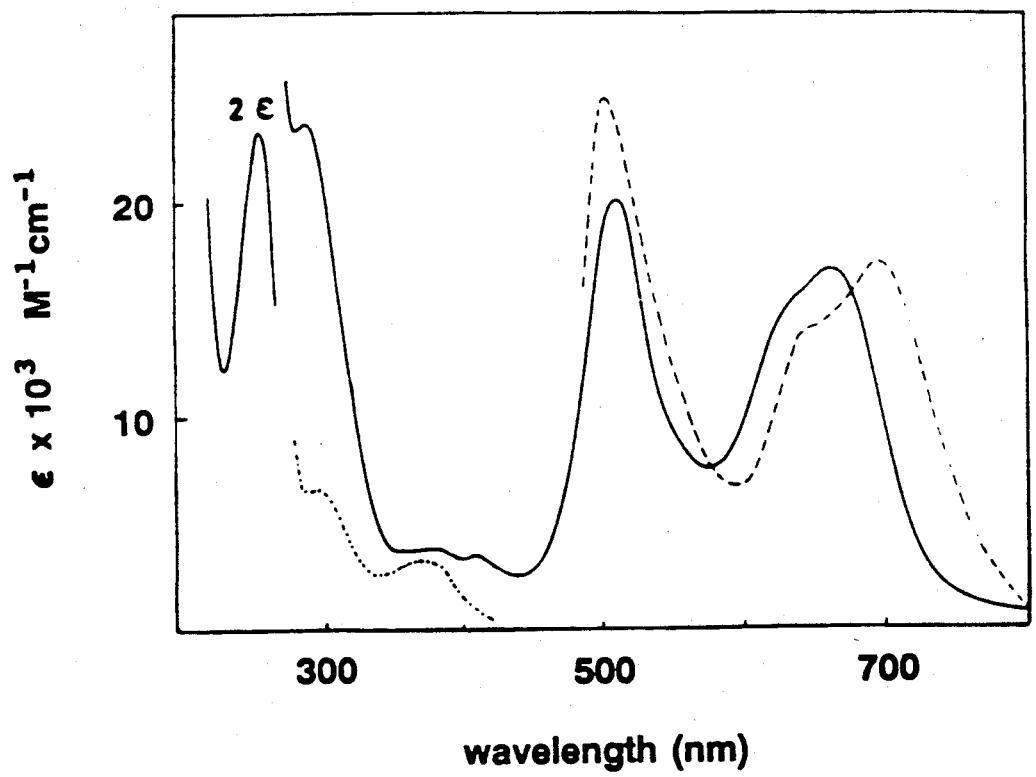
FIG. 2: Absorption spectra of $Ru(phi)_3^{2+}$ in ethanol (—) and from 500 to 800 nm in HMPA(--). Absorption spectrum of $Zn(phi)Cl_2$ in DMF from 275 to 425 nm (..) is not to scale.

Ru(phi)₃Cl₂ is a vivid purple molecule with a rich absorption spectrum. A representation of its structure is shown in FIG. 1. The electronic spectrum of Ru(phi)₃²⁻, along with that of Zn(phi)Cl₂, is given in FIG. 2. The ruthenium complex shows three intense transitions in the visible region, at 510 nm ($\epsilon_{max}$=18 200 M⁻¹ cm⁻¹) Assignment of the transitions is aided by comparison to the spectrum of Zn(phi)Cl₂, which, by virtue of its d¹⁰ electron configuration, exhibits only $\pi$-$\pi$* transitions and should approximate the electronic behavior of the air-sensitive phenanthrenequinone diimine ligand. As can be seen in FIG. 2, the zinc complex shares with the ruthenium species transitions at 380 nm ($\epsilon_{Zn}$=2000 M⁻¹ cm⁻¹, $\epsilon_{Ru}$=4000 M⁻¹ cm⁻¹), 300 nm ($\epsilon_{Zn}$=4500 M⁻¹ cm⁻¹, $\epsilon_{Ru}$=22 500 M⁻¹ cm⁻¹), and 256 nm ($\epsilon_{Zn}$=50000 M⁻¹ cm⁻¹, $\epsilon_{Ru}$=45000 M⁻¹ cm⁻¹). These higher energy [Ru(phi)₃]Cl₂ transitions may therefore by assigned as $\pi$-$\pi$* on the basis of their similarity to those of Zn(phi)Cl₂. The broad intense transitions for the ruthenium complex at longer wavelengths (510, 640, and 660 nm) may be assigned in contrast as charge-transfer transitions.

Figure 3:
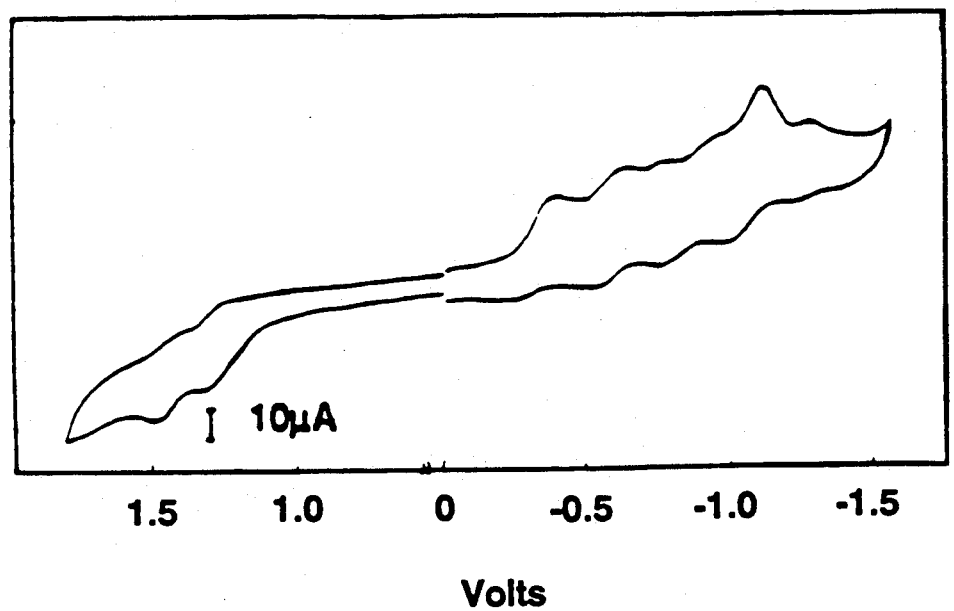
FIG. 3: Cyclic voltammogram of $Ru(phi)_3(PF_6)_2$ in acetonitrile. All measurements taken at 100 mV/s scan speed. V versus SCE. The featureless oxidative scan between 0 and 0.5 V is not shown.

Cyclic voltammetry reveals multiple electrochemical reduction steps and oxidations in the ruthenium complex (FIG. 3). Electrochemical oxidation of [Ru(phi)₃](PF₆)₂ in acetonitrile is irreversible. Oxidation potentials of 1.23 and 1.42 eV versus SCE were observed at a scan speed of 100 mV/s. Of the six reduction potentials observed at −0.38, −0.60, −0.75, −0.95, −1.11, and −1.28 eV, only those at −0.60, −1.11 and −1.28 eV were found to be reversible. A standard of [Ru(phi)₃](PF₆)₂ showed first redox potentials of −1.31 and +1.30 V, respectively. As may be expected, the increased $\pi$-acidity of the phi ligand compared to that of bipyridyl or phenanthroline leads to substantially decreased reduction potentials for the Ru(phi)₃⁻² complex.

Possible emission from [Ru(phi)₃]Cl₂ was monitored at pH 1-11, in various solvents and at 77 K. No emission was observed from 350 to 800 nm. The lack of emission is understandable in view of the short lifetime of the excited state and the transient excited-state absorption spectrum ($\lambda_{max}$=440 nm), measured by flash photolysis, revealed a lifetime of ≦6 ns, the length of the laser pulse.

Figure 4:
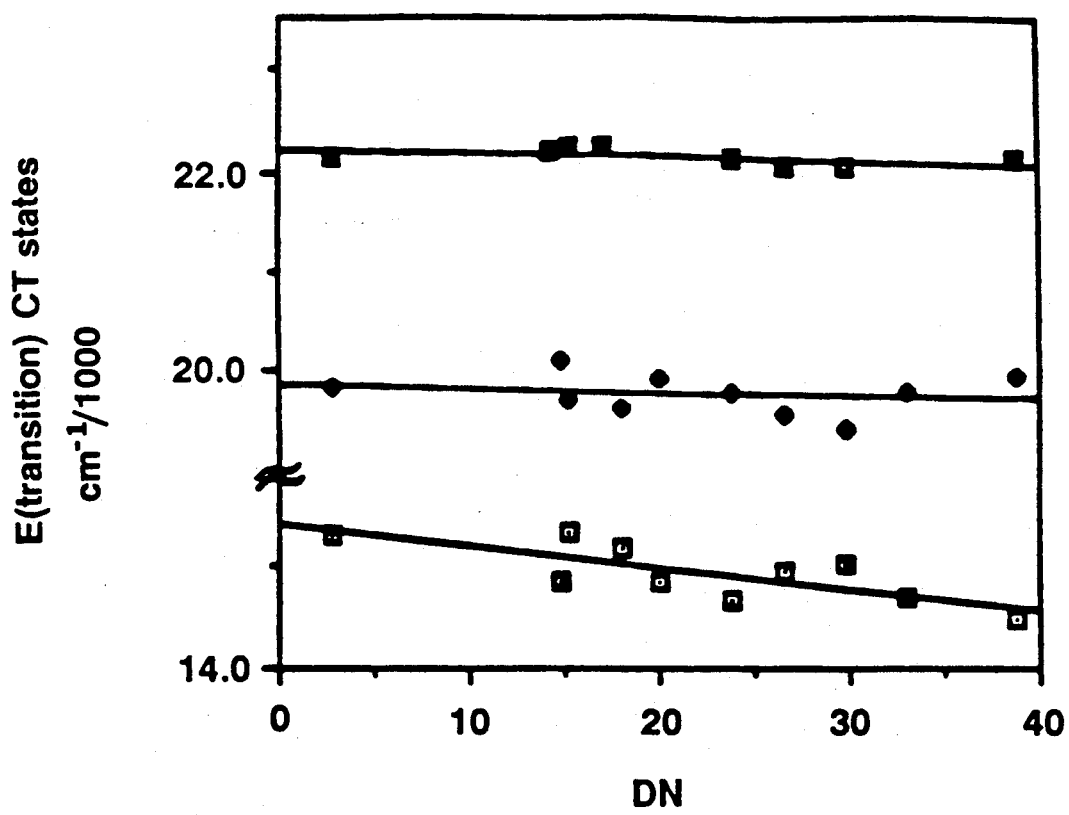
FIG. 4: Plot of hydrogen-bonding solvatochromism as measured by the shift in energy of CT bands with donor number (DN): (■) $Ru(bpy)_3^{2+}$, $y=22.2-0.004x$; (♦) $Ru(phi)_3Cl_2$, CT3, $y=19.8-0.004x$; (□) $Ru(phi)_3Cl_2$, CT1, $y=15.4-0.02x$. Measurements were obtained in the following solvent array (DN is parentheses): nitromethane (2.7), dioxane (14.8), propylene carbonate (15.1), water (18.0), THF (20.0), tributyl phosphate (23.7), DMF (26.6), DMSO (29.8), pyridine (33.1), HMPA (38.8).
Figure 5A:
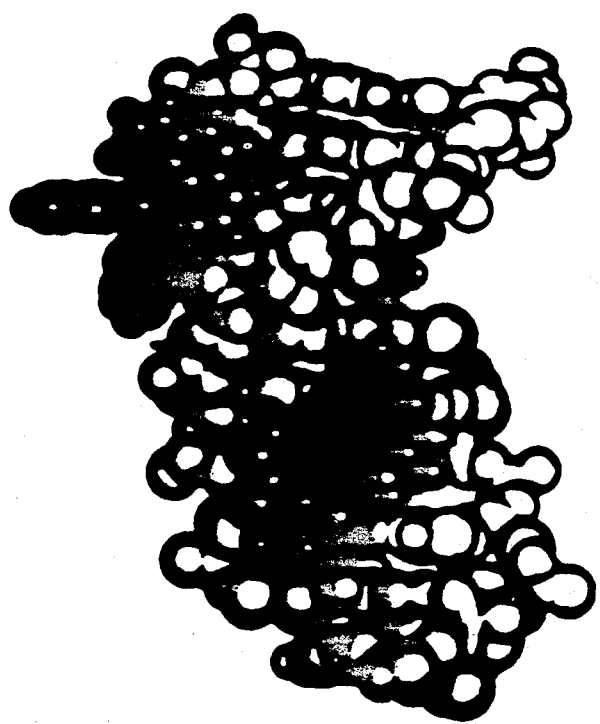
FIGS. 5A and 5B: Models for the two non-covalent binding interactions of the octahedral metal complexes with DNA. Shown are $\Delta$-$Ru(phen)_3^{2+}$ (bottom) intercalated into the major groove and $\Lambda$-$Ru(phen)_3^{2+}$ (top) surface-bound against the minor groove of the DNA helix. FIG. B displays the same models after a 90° rotation about the helical axis. Graphics were performed on an Evans and Sutherland PS390 terminal using the Macromdel program.
Figure 5B:
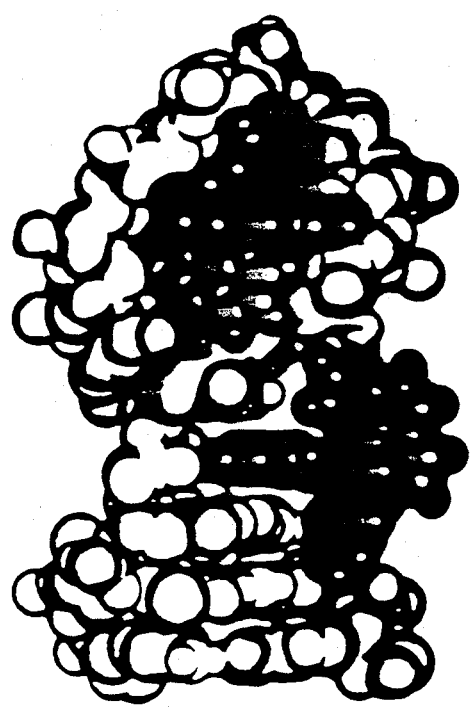
Figure 6A:
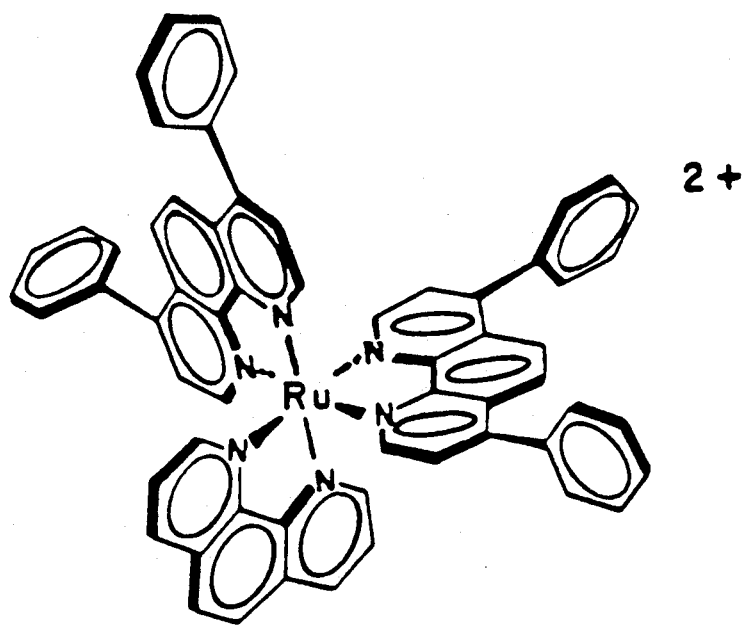
FIGS. 6A-6D: Illustration of several mixed ligand complexes: $\Lambda$-$Ru(DIP)_2phen^{2+}$ (top left); $\Delta$-$Ru(phen)_3^{2+}$ (top right); $\Lambda$-$Ru(phen)_2phi^{2+}$ (bottom left); $\Delta$-$Ru(bpy)_2phen^{2+}$ (bottom right).
Figure 6B:
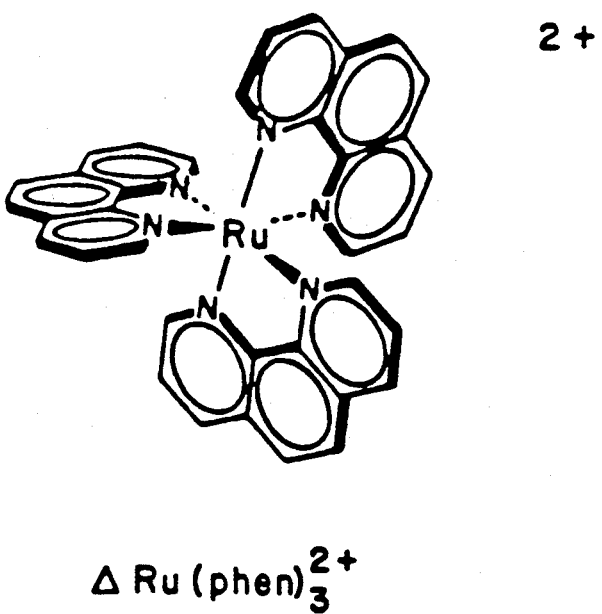
Figure 6C:
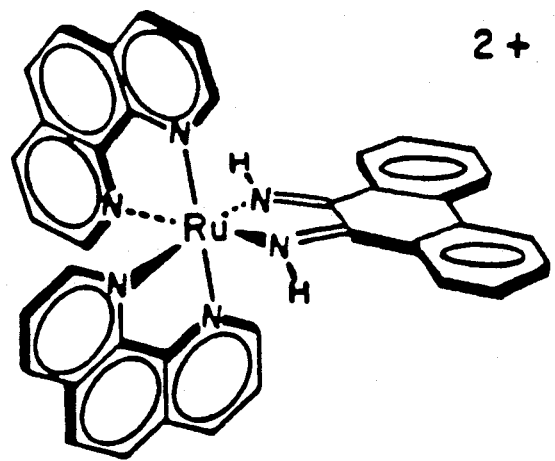
Figure 6D:
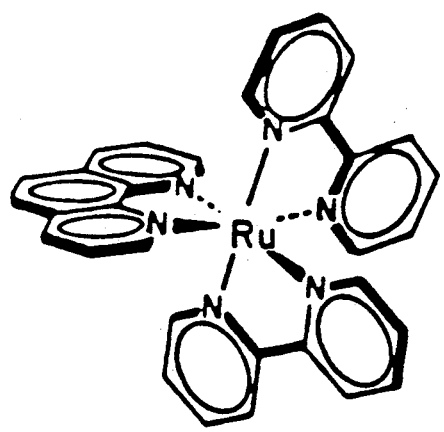
Figure 6D:
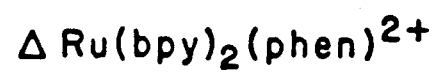
Figure 7A:
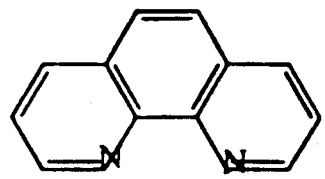
FIGS. 7A-7F: Ligands used for the synthesis of mixed-ligand ruthenium complexes.
Figure 7B:
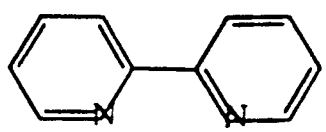
Figure 7C:
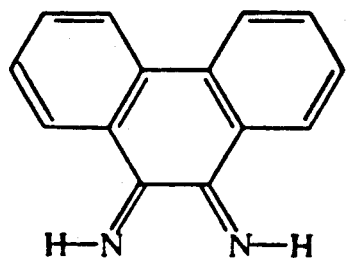
Figure 7D:
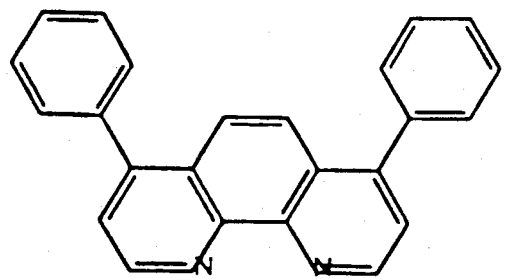
Figure 7E:
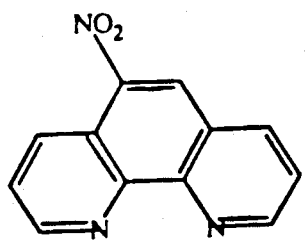
Figure 7F:
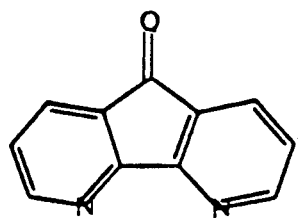

The excited-state energy fo Ru(phi)₃⁻² appears to be highly dependent on the molecular environment. Small changes in pH, salt concentration, or solvent lead to large variations in the $\lambda_{max}$ of the charge-transfer (CT) bands. As can be seen in FIG. 4, this solvent dependence contrasts sharply the little solvatochromism observed for Ru(bpy)₃²⁺ (15). Most significantly, the energy of the 660-nm charge-transfer band (CT1 in ethanol) decreases linearly as the Lewis base character, or donor number (DN), (16) of the solvent increases. CT1 is one component of a double-structured absorption commonly found among ruthenium diimine complexes. Curiously, it is only the CT1 absorption and not its companion band at 640 nm (CT2) that displays hydrogen-bonding solvatochromism with Lewis bases. The two seemingly fused bands at low DN seem to move apart in energy as the DN increases, and the CT1 band red shifts to as much as 700 nm in HMPA. The energy of the 510-nm band (CT3) fluctuates with solvent, but like the MLCT bands of Ru(bpy)₃²⁻, this fluctuation is not linear with DN. Thus the CT2 and CT3 transitions of Ru(phi)$_3^{2+}$ are not sensitive to hydrogen bonding and must be of distinctly different character than the lowest energy CT1 band, which fluctuates between 650 and 700 nm as the strength of hydrogen-bonding interactions increases. Such solvatochromic behavior lends itself well to the application of the complex as a photophysical probe, because the energy of bands like CT1 becomes a sensitive indicator of the metal environment and possible hydrogen bonding interactions.

The spectral characteristics of Ru(phi)$_3^{2+}$ reveal several novel and unexpected features of the electronic structure of the complex. Perhaps most interesting is the lowest energy charge-transfer transition, CT1, centered at 660 nm in ethanolic solution. This transi-tion is among the lowest energy transitions thus far observed for monomeric ruthenium (II) species. (17) Blue ruthenium species have been reported previously, (14) but while their structures have remained elusive, all have been formulated as multinuclear species. The low-energy transitions in Ru(phi)$_3^{2+}$ may arise in part from the coordination of the highly delocalized phi ligand. Coordinated phenazines and dicyanomethylene-substituted phenanthrolines represent other applications of an extended $\pi$-framework, yet for those the charge-transfer transitions are centered at wavelengths more than 100 nm shorter. (18)

Most curious however is the comparison to the mixed-ligand complex (7) Ru(bpy)$_2$phi$^{2+}$. The mixed species shows charge-transfer transitions at 450 and 525 nm, which may be attributed to localized charge transfer onto the bpy and phi ligands, respectively, in the excited state. Spectra of mixed-ligand polypyridyl complexes of ruthenium (II) have in general been the simple sum of spectra for the tris-chelate complexes, since the metal to ligand charge-transfer is localized in these systems. (19) Also surprising is the short excited-state lifetime of Ru(phi)$_3^{2+}$ and the solvent dependence of one of the low-energy transitions.

The distinctive spectral characteristics of Ru(phi)$_3^{2+}$ might be understandable on the basis of a delocalized charge transfer onto the three ligands. The sequential lowering of the energy of the transition (150 nm change in wavelength) (20) with increasing substitution of phi ligands suggests such delocalization and stands in sharp contrast to spectral characteristics of the localized bipyridyl system, where the intensity rises but the energy of the charge-transfer band does not shift appreciably with increasing bpy substitution. This delocalization may also explain the intense low-energy transitions observed in other tris($\alpha$-diimine) complexes. (8, 21) The delocalized framework may, finaly, also account for the short excited-state lifetime of the complex, owing to large spin-orbit coupling that would be inherent in a completely delocalized system. Alternatively, the excited state is sufficiently low in energy that it may be rapidly deactivated by coupling to the ground state.

In summary, Ru(phi)$_3^{2+}$ displays intense, unusual transitions at low energies. On the basis of a comparison with a zinc analogue, the transitions may be described as charge transfer in character. By comparison with a mixed-ligand complexes of phi, a delocalized charge-transfer transition is suggested. Finally the dependence of the transitions on hydrogen bonding in addition to the rich intensity at long wavelengths renders the complex useful as a biophysical probe.

II. Synthesis and Characterization of Mixed Ligands Complexes

A subset of the complexes examined is shown schematically in FIG. 6. The complexes examined are coordinatively saturated and rigid in structure. All are dications and therefore the electrostatic component of the binding is a constant across the series (to first approximation given some size variation). By varying ligands and ligand substituents in the complexes in a systematic fashion, as illustrated in FIG. 6, and comparing binding parameters for the series, the contributions of the different ligand functionalities and sizes to the binding interactions with DNA can be determined. The ligands employed in this study are shown in FIG. 7. The study of the mixed ligand complexes with DNA offers the opportunity to explore systematically how such factors as molecular shape and hydrogen bonding stabilize small molecules on DNA.

Materials: RuCl$_3$.3H$_2$O was purchased from Engelhard Co. Ligands (Aldrich) were checked for purity by NMR and recrystallized if necessary.

Ru(bpy)$_2$(phen)]Cl$_2$.[Ru(phen)$_2$(bpy)]Cl$_2$: These complexes were synthesized by methods as described previously. (15) Ru((phen)$_2$(DIP)]CL$_2$: Ru(phen)$_2$Cl$_2$(1 mmole) was added to 1 equivalent of 4,7-diphenyl-1,10-phenanthroline (DIP) and refluxed in 14 ml 75% ethanol/water for 30 minutes. The produce was isolated as the CIO$_4$— salt for chromatography on cellulose (10% CHCl$_3$/hexane) and converted to the chloride salt by ion exchange. NMR(DMSO): 8.79 (4dd), 8.4 (4s), 8.24 (2d), 8.22 (2s), 8.16(2d), 8.08 (2d), 7.83 (2dd), 7.78 (2dd), 7.75(2d), 7.63(10m); FABMS ion mass: 794 [Ru(phen)$_2$(DIP)]$^{2+}$, 614[Ru(pen)(DIP)]$^{2+}$.

Ru(bpy)$_2$(DIP)]Cl$_2$: Synthesized as described above, using Ru(bpy)$_2$Cl$_2$ rather than Ru(phen)$_2$Cl$_2$ as starting material.

Ru(DIP)$_2$(phen)]Cl$_2$: Ru(DIP)$_2$Cl$_2$ was refluxed in ethanol with one equivalent of phenanthroline. The produce was purified by cellulose chromatography. The Ru(DIP)$_2$Cl$_2$ starting material, like the other bis(polypyridyl) complexes, was readily prepared by dissolving 3 mmoles RuCl$_3$.3H$_2$O, 30 mmoles LiCl and 6 mmoles DIP ligand in 100 ml DMF and refluxing for four hours. Ther reaction mixture was stripped of solvent and the product precipitated from ethanol/water. Further purification was as for [Ru(phen)$_2$(DIP)]Cl$_2$.:NMR(DMSO): 8.82(2d) 8.42(2s), 8.34(2d), 8.25(4s), 8.23(2d), 8.18(2d), 7.87(2dd), 7.80(2d), 7.74(2d), 7.69 (20m); FABMS ion mass: 946 [Ru(DIP)$_2$(phen)]$^{2+}$,766 [Ru(DIP)$_2$]$^{2+}$, 614 [Ru(DIP)(phen)]$^{2+}$.

[Ru(5-nitrophenanthroline)$_3$)]Cl$_2$: Synthesized as described by Lin et al. (37)

[Ru(phe)$_2$(4,5-diazafluorene-9-one)]Cl$_2$: One equivalent of 4,5-diazafluorene-9-one and a suspension of one mmole Ru(phen)$_2$Cl$_2$ in 30 ml were refluxed in wet ethanol for four hours and recystallized from acetone/heptane. The 4,5-diazafluorene-9-one ligand was syntheisized as described by Henderson et al. (38) NMR (CD$_3$CN): 8.71 ppm (2 dd), 8.61 (2 dd), 8.55 (2 dd), 8.25 (4 d), 8.10 (2d), 8.03 (2 dd), 7.88 (2m), 7.59(4m), 7.39(2m); FABMS ion mass: 644 [Ru(phen)$_2$(flone)]$^{2+}$.

[Ru(bpy)$_2$(phi)]Cl$_2$: This complex was prepared as previousuly reported by Belser et al. (34). NMR (DMSO): 13.67 ppm (2,s N—H), 8.68 (4d), 8.60 (2d), 8.35(2d), 8.05(2t), 8.0 (2t), 7.75 (2d), 7.57(2t), 7.43(8m): FABMS ion mass: 620 [Ru(bpy)$_2$(phi)]$^{2+}$, 465 [Ru(b-py)(phi)]$^{2+}$, 414 [Ru(bpy)$_2$]$^{2+}$, 257 [Ru(bpy)]$^{2+}$. Anal.

Calcd for [Ru(bpy)₂(phi)](PF₆)₂: C:44.90; H: 2.90; N: 9.20; found C: 44.62; H: 3.02; H: 8.9. A crystal structure (data not shown), determined by x-ray diffraction analysis, confirms the coordination geometry of this species.

[Ru(phen)₂(phi)]Cl₂: As with the synthesis of Ru(bpy)₂(phi)Cl₂, this compound was prepared by refluxing 0.19 mmoles Ru(phen)₂Cl₂, 1.2 ml 0.1M NaOH and 0.7 mmoles diaminophenanthrene in 5 ml H₂O containing a catalytic amount of zinc dust. After one hour, 3 ml EtOH was added and the resultant purple solution was air oxidized for 16 hours in the presence of 0.5 ml NH₄OH. The final red solution was extracted with diethyl ether to remove organic impurities and precipitated with KCl. NMR (DMSO): 13.81 ppm (2,s N—H), 8.86(2d), 8.75(2d), 8.63 (2d), 8.55(4m), 8.37 (4s), 8.05(1d), 7.95(1d), 7.85 (1d), 7.80 (2d), 7.78(1d), 7.73(2t), 7.57(2t); FABMS ion mass: 667 [Ru(phen)₂(phi)]²⁻, 488 [Ru(phen)(phi)]²⁻, 460 [Ru(phen)₂]²⁻, 282 [Ru(phen)]²⁻. Anal. Calcd for Ru(phen)₂(phi)Cl₂.KCl.5·H₂O: C:50:50; H:4.02; N:9:30; Found: C:50.11; H: 4.04; N:9.84.

[Ru(phi)₂(bpy)]Cl₂: Obtained by a synthesis identical to that for [Ru(Benzoquinonediimine)₂(bpy)]Cl₂. (34) 9,10-diaminophenanthrene was used as the ligand substrate instead of diaminobenzene. In addition, solvent for the final air oxidation step of this compound was 50% ethanol/water rather than pure water. Like the other phi-containing compounds, this complex was first isolated as the PF6- salt and converted to the chloride by precipitation with KCl or ion exchange on AG MP-1 resin from Bio-Rad. NMR (DMSO): 14.16 ppm (2s N—H), 12.87 (2s N-H), 8.78 (4t), 8.6(2d), 8.52 (4d), 8.20(4m), 7.75(4t), 7.65(6m); FABMS ion mass: 669 [Ru(phi)₂(bpy)]²⁻, 514[Ru(phi)₂]²⁻, 464 [Ru(phi)(bpy)]²⁻, 307 [Ru(phi)²⁻. Anal Calcd. for Ru(phi)₂(bpy)Cl₂.6HO₂) C:53.78; H: 4.76; N:9.90. Found: C:53.84; H: 496; N:9.02.

METHODS

Instrumentation: NMR spectra were recorded on a Varian VXR-300MHz spectrometer. FABMS were performed using a VG Analytical 7070EQ Mass Spectrometer (34), and elemental analyses were done by Galbraith Laboratories in Nashville, Tennessee. UV-Visible absorbance spectra were recorded on a Varian CARY-219 absorbance spectrophotometer. Extinction coefficients for the compounds were determined versus ruthenium concentrations obtained by atomic absorption spectroscopy with known ruthenium standards. [Ru(bpy)₃]Cl₂ solutions were also employed for these determinations as an internal standard. A Varian AA-875 atomic absorption spectrophotometer was used for these determinations.

Emission spectra were measured on a Perkin-Elmer LS-5 fluorescence spectrometer. The samples were excited at their corresponding isosbestic points. All the measurements were made at 20° C. in a thermostatted cuvette holder with 3 nm entrance slit and 10 nm exit slit. Ruthenium solutions employed were 7 μM in concentration and calf thymus DNA was added to a ratio of 40:1 nucleotide/metal; ruthenium-DNA solutions were allowed to incubate for 15 minutes before enhanced spectra were recorded. The emission enhancement factors were measured by comparing the intensities at the emission spectral maxima in the absence and presence of DNA, under similar conditions.

The luminescence lifetime measurements were done on a PRA SPC (single photon countining) spectrometer with some minor modifications. The samples were excited with a nitrogen filled thyratron gated flash lamp and the data were collected using a Tracor Northern 1710 multichannel analyser. The data were then transferred to a PDP-11/03 computer and deconvoluted with PRA sofware. The validity of the convergent biexponential fits was checked using four different tests. A concentrated solution of DNA (5mM DNA-phosphate) in buffer was added to a solution of the metal complex (4 μM) in buffer and allowed to equilibrate. Lifetimes of the samples were measured 0.5 hr after the metal complexes were mixed with DNA. All measurements were made at 20° C. and under air saturated conditions.

Excited state resonance Raman spectra were run on a home-built Raman spectrometer with an intensified multichannel detector. (40) The samples were excited by a QuantaRay, Q-switched, Nd-YAG laser (DCR-2, FWHM =6 ns, 5 mJ per pulse at 355 nm). The laser power was high enough to saturate the excited state population and also to scatter off from the excited state formed during the laser pulse-width. The sample solution was pumped through a nozzle to form a smooth thin jet which was intercepted by the laser. The back scattered light was collected at a small angle to the pump beam and focused onto the entrance slit of the Spex triple-mate spectrograph. The third stage of the spectrograph contained at 2400 grooves/mm grating to provide −2 cm⁻¹ resolution for the Raman experiments. The entire experiment was run by a home made menu-driven program with customized graphics written in Heminway Basic. The spectra were calibrated using the known spectrum of Ru(bpy)₃²⁻*. (41) To a solution of calf thymus DNA (1 mM) was added Ru(bpy)₂DIP²⁺(40 μM) and the solution was left to equilibrate for 0.5 hour. The solution was then circulated as a thin, smooth and slow stream. No degradation in the sample, as determined by opical absorption, was observed after recording of the Raman spectrum under these conditions.

Measurement of Solubilities: Solubilities of the compounds were measured by preparing saturated solutions of metal complex in buffer (50 mM NaCl, 5 mM Tris, pH 7.5) and allowing the suspensions to equilibrate for 24 hours at 25 C. After that time, the solutions were spun down in an Eppendorff microcentrifuge at 15,000 rev./min for 2 minutes and the supernatant was carefully removed by pipette. After dilution, the ruthenium concentrations were measured by UV-visible absorbance.

Equilibrium Dialysis: Equilibrium dialysis of the racemic metal complexes was performed against calf-thymus DNA using procedures described previously (30) The buffer used was 5 mM Tris, 50 mM NaCl at pH 7.5. Samples were agitated on a shaker bath during equilibration which occurred after three to five days, as determined by control samples containing no DNA. After equilibration, volumes of liquid inside and outside the dialysis bags were determined (approximately 1 and 3 mls, respectively) and circular dichroism of the dialysate was measured on a Jasco J-40 spectropolarimeter. Final ruthenium concentration inside and outside the bags were measured by visible absorbance. Data analysis was performed on a VAX-780 using non-linear least squares analysis.

Topoisomerase Assay: In a typical experiment, pBR322 DNA dinner (0.47 μg, BRL) was incubated at 37 C for 1h with 2 to 4 units of Topoisomerase I (from calf thymus, BRL) in reaction mixtures containing 5 mM Tris-HCl, pH 7.2, 50 mM NaCl, 1 mM MgCl$_2$, and from 1 to 100 μM ruthenium complex (50 ml total volume). Following incubation, the mixtures were ethanol precipitated (200 ml ethanol) at −20 C, centrifuged, and resuspended in 20 ml buffer (no Mg$^{2+}$). The samples were then electrophoresed in 1% agarose for 4 to 6 h. Photographic negatives of the agarose gels were scanned on an LKB model 2202 ultroscan laser densitometer. The unwinding angles were determined graphically from plots of −τ, where τ equals the number of superhelical turns, versus the concentration of bound ruthenium complex, as described by Keller, (42) using the following equation: (43)

$$\sigma = 20 r_c (\phi/360) = r_c \phi/18$$

pel equation (45) governing random non-cooperative binding to a lattice.

$$2r/c_f = K_b(1-2/r)[(1-2/r)/[1-2(/-1)r]]^{-1}$$

where r is the ratio of bound concentration of ruthenium to the concentration of DNA-phosphate, $c_f$ is the concentration of ruthenium free in solution, $K_b$ is the intrinsic binding constant, and the integer /, which measures the degree of anti-cooperativity, is the size of a binding site in base pairs. The curves shown reflect the best fit after variation of two parameters: the intrinsic binding constant, $K_b$, and binding site size, /. For those complexes where cooperativity was observed, the equation (45) incorporating a cooperativity parameter was used. The vales obtained are summarized in Table 1.

TABLE 1

| | DNA BINDING PARAMETERS FOR MIXED LIGAND COMPLEXES OF RUTHENIUM(II) | | | | | |
|---|---|---|---|---|---|---|
| COMPLEX | $K_b(M^{-1}) \times 10^3)^a$ equilibrium dialysis | $K_b(M^{-1}) \times 10^3)^b$ by absorption titration | Site Size$^c$ (base pairs) | Unwinding concentration$^d$ (μM) | Unwinding Angle$^e$ (degrees) | Enantio-selectivity$^f$ |
| Ru(bpy)$_3$Cl$_2$ | 0.7 (.13) | h | 6-12 | 650 | | none |
| Ru(bpy)$_2$(phen)Cl$_2$ | 0.7 (.07) | h | 10-14 | 69 | | Δ |
| Ru(phen)$_2$(bpy)Cl$_2$ | 2.4 (.4) | 4.6 (1.0) | 5-7 | 11 | 18 | Δ |
| Ru(phen)$_3$Cl$_2$ | 3.1 (.1) | 5.5 (.99) | 4 | 9 | 19 | Δ |
| Ru(5-NO$_2$phen)$_3$Cl$_2$ | 1.0 (.1) | h | 8-12 | i | | Δ |
| Ru(phen)$_2$(flone)Cl$_2$ | 2.1 (.2) | h | 9-12 | i | | none |
| Ru(bpy)$_2$(DIP)Cl$_2$ | 1.7 (.3) | h | 12-18 | 170 | | Δ |
| Ru(phen)$_2$(DIP)Cl$_2$ | 2.5 (1.0) | 11.2 (.99) | cooperative | 9 | | Δ |
| Ru(DIP)$_2$(phen)Cl$_2$ | 10.1 (3) | 11.1 (.99) | cooperative | j | j | Δ |
| Ru(phi)$_2$(bpy)Cl$_2$ | 17.6 (−) | 24.4 (.98) | cooperative | 0.6 | j | k |
| Ru(phen)$_2$(phi)Cl$_2$ | 46. (6)$^g$ 110. (37)$^g$ | 46.8 (.99) | 2-3 | 1.2 | 26$^g$ | l |
| Ru(bpy)$_2$(phi)Cl$_2$ | 160. (17) | 48.0 (.99) | 4 | 1.1 | 17 | l |

$^a$Standard deviations are given in parentheses
$^b$Correlation coefficients between observed and calculated values are given in parentheses. Values for $K_b$ have been calculated as described in the text
$^c$For this range of site sizes, less than 1% variation in correlation coefficient and standard deviation in $K_b$ is found. For the lowest site size given, best correlation and the lowest standard deviation in $K_b$ are obtained.
$^d$Concentration of ruthenium complex needed to unwind 11 of 22 supercoils. [DNA] = 47 μM for assays of phi-containing complexes and 31.5 μM for all others
$^e$Unwinding angles represent the number of degrees by which one molecule of bound complex unwinds the DNA helical duplex. Values are calculated with some certainty only for those complexes where the binding is otherwise well-behaved.
$^f$Deltas represent an enantiomeric preference for the Δ isomer in binding to DNA
$^g$The lower binding constant and site size given result from fitting only those points where r > 0.08. The higher binding constant given results from inclusion of all points. Although the fit with all points included is poorer, it is probably a better overall estimate of binding affinity.
h At the extremely low levels of binding obtained with these complexes, changes in the absorption spectrum were too small to allow for significant determinations.
i Measurements were not conducted on this complex
j Measurement could not be performed due to the poor solubility of the complex.
k A small circular dichroism was occasionally observed in the dialysate.
l Although the dialysate showed a strong circular dichroism, and thus a clear enantiomeric selectivity in binding to DNA exists, the absolute configurations for the phi complexes cannot be inferred from simple comparison to phenanthroline complexes.

where σ is the superhelical density of the plasmid, $r_c$ is the amount of metal complex ions bound per nucleotide when all of the superhelices are removed, and φ is the unwinding angle. Bound concentrations were determined by interpolation from the Scatchard plots of equilibrium dialysis data.

RESULTS

Figure 8B:
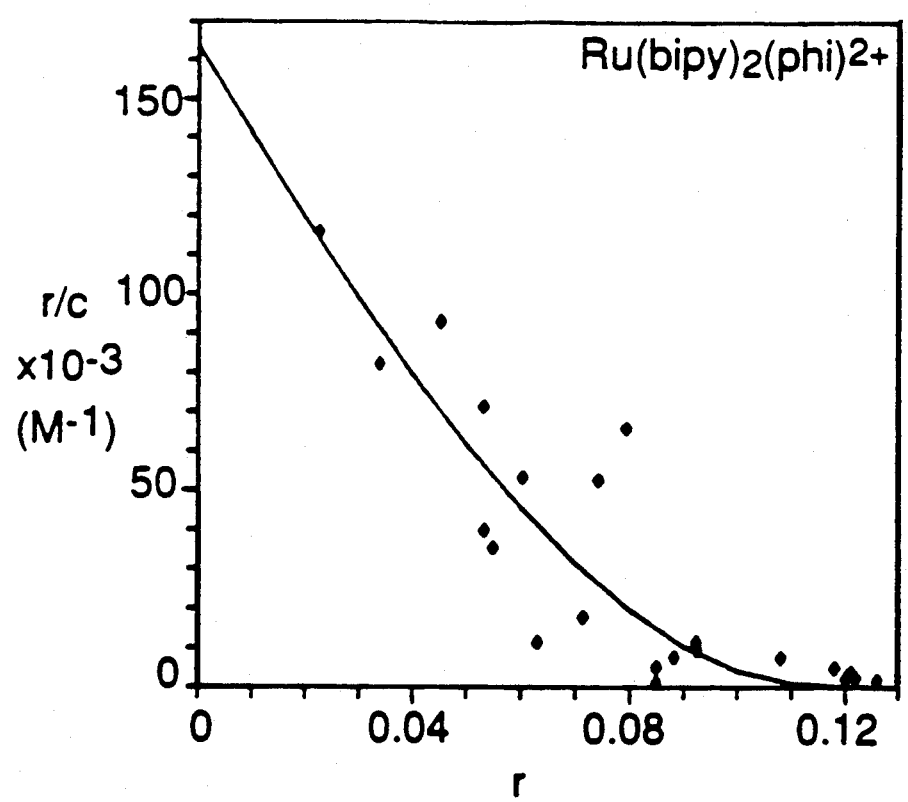
FIGS. 8A$_1$-8A$_7$and 8B: Representative Scatchard plots of binding isotherms for mixed-ligand complexes of ruthenium(II) with calf thymus DNA in buffer at 22 C, where r is the ratio of bound ruthenium to nucleotide concentrations and C is the concentration of free ruthenium. The solid lines are the best fits to the McGhee and von Hippel equation (45) governing non-cooperative binding to the helix.

Equilibrium Dialysis: Esquilibrium binding constants for the metal complexes with DNA may be determined classically by equilibrium dialysis. Calf thymus DNA was dialyzed against the series of mixed ligand complexes using a broad range of ruthenium concentrations. Data are shown in FIG. 8 for the eight complexes which showed noncooperative binding to the polynucleotide. The results have been plotted according to Scatchard (44), where r is the ratio of bound metal to DNA-phosphate concentration, and $c_f$ is the concentration of free metal complex. The data were fit by non-linear least squares analysis to the McGhee and von Hip- For the complexes shown, the intrinsic binding constant is seen to vary over more than two orders of magnitude. The highest binding affinity is seen for complexes which contain the phi ligand. Other variations, though of a smaller magnitude, are apparent as a function of increasing size and hydrophobicity. For example, for the series Ru(bpy)$_3$$^{2+}$, Ru(bpy)$_2$(phen)$^{2+}$, Ru(bpy)$_2$(DIP)$^{2+}$, and Ru(bpy)$_2$(phi)$^{2+}$, we find $K_b$ values of 0.7×10$^3$, 0.7×10$^3$, 1.7×10$^3$, and 1.6×10$^5$ M$^{-1}$, respectively. The data for the all the complexes fit reasonably well to a random non-cooperative model. Site sizes are found to vary between 2 and 12 base pairs, but values obtained for complexes with low binding affinity (K<2×10$^3$M$^{-1}$) have a high associated uncertainty.

The bulkier and more hydrophobic complexes Ru(phen)$_2$(DIP)$^{2+}$, Ru(DIP)$_2$(phen)$^{2-}$ and Ru(phi)$_2$(bpy)$^{2+}$ all showed curves indicative of cooperative binding. This observation is understandable, since these complexes tend to aggregate in solution. Thus the equilibrium involves not only bound and free monomer complexes but those involving self-stacked dimers (or even larger aggregates). Furthermore, a similar aggregation of the complexes along the DNA strands is likely. Some samples actually showed precipitation, and these were not included. The extensive aggregation of $Rr(DIP)_3^{2+}$ and $Ru(phi)_3^{2+}$ completely precluded their incorporation in these studies.

Equilibrium dialysis experiments additionally offer the opportunity to examine any enantiomeric selectivities associated with binding. After dialysis of the DNA against the racemic mixture, optical activity observed in the dialysate reflects an enrichment in the dialysate in the less favored enantiomer. For most of the complexes, optical activity was found in the dialysate. Values for the extent of enantiomeric selectivity could not be quantitated in the absence of determinations of DE and assignments of absolute configuration. Assuming that the signs of the circular dichroism in the ultraviolet ligand bands are the same for these ligands as that for the parent phenanthroline complex, (46) we have assigned the absolute configuration of these complexes by comparison to spectra for enantiomers of $Ru(phen)_3^{2+}$ and have compared levels of enantioselectivity qualitatively through measurements of circular dichroic intensity per ruthenium bound. Based upon these assumptions, we find enantionmeric selectivities for the polypyridyl complexes to reflect an enrichment in the isomer in the dialysate and the preferential binding of the isomer to the right-handed DNA. This observation is consistent with the preferential intercalation of isomers found earlier for $Ru(phen)_3^{2+}$ in right-handed B-DNA. (29) We may also compare relative enantioselctivities for different ancillary ligands. For the pairs, $Ru(phen)_2phi^{2+}$ versus $Ru(bpy)_2phi^{2+}$, for example, the intensity in circular dichroism per ruthenium bound is more than three times greater with phen as the ancillary ligand than with bpy. The same comparison may be seen qualitatively between $Ru(phen)_2DIP^{2+}$ and $Ru(bpy)_2DIP^{2+}$. The exceptions, where no enantiomeric discrimination is apparent, are $Ru(phi)_2bpy^{2+}$, $Ru(bpy)_3^{2+}$ and $Ru(phen)_2(flone)^{2+}$. For $Ru(phi)_2bpy^{2+}$, aggregation of the complex and its poor solubility made the determinations problematic. In the cases of $Ru(bpy)_3^{2+}$ and $Ru(phen)_2(flone)^{2+}$, the low levels of binding and small size of the complex may preclude observation of any selectivity.

Spectroscopic Changes on Binding to DNA: The complexes all possess intense optical absorption owing to their well-characterized metal to ligand charge transfer band. Furthermore, for all the complexes, this electronic transition is perturbed on binding to DNA. Table 2 summarizes the spectroscopic properties of the complexes and some of the changes observed.

TABLE 2

SPECTROSCOPIC PROPERTIES ON BINDING TO DNA

| COMPLEX | Absorption $\lambda_{max}$ (nm) | | | Emission $\lambda_{max}$ (nm) | | | $\epsilon_{free}$ (M-1 cm-1) | Emission Enhancment (I/I₀) | Emission Lifetime (nanoseconds) | |
|---|---|---|---|---|---|---|---|---|---|---|
| | free | bound | Δλ | free | bound | Δλ | | | free | bound[d] |
| $Ru(bpy)_3^{2+}$ | 450 | 450 | 0 | 615 | 618 | 3 | 14,600 | 1.06 | 420 | |
| $Ru(bpy)_2(phen)^{2+}$ | 452 | 452 | 0 | 611 | 602 | −9 | 16,000 | 1.12 | 450 | 430 ± 30(1) |
| | | | | | | | | | | 2100 ± 300(2) |
| $Ru(phen)_2(bpy)^{2+}$ | 446 | 448 | 2 | 608 | 604 | −4 | 19,200 | 1.43 | 555 | 530 ± 30(1) |
| | | | | | | | | | | 2100 ± 260(2) |
| $Ru(phen)_3^{2+}$ | 443 | 445 | 2 | 591 | 593 | 2 | 20,000 | 1.87 | 530 | 630 ± 70(1) |
| | | | | | | | | | | 2300 ± 620(2) |
| $Ru(5-NO2phen)_3^{2+}$ | 450 | 454 | 4 | b | — | | 20,000[c] | — | | — |
| $Ru(phen)_2(flone)^{2+}$ | 436 | 436 | 0 | b | — | | 18,800 | — | | — |
| $Ru(bpy)_2(DIP)^{2+}$ | 454 | 454 | 0 | 615 | 621 | 6 | 18,600 | 1.13 | 700 | 640 ± 40(1) |
| | | | | | | | | | | 4700 ± 600(2) |
| $Ru(phen)_2(DIP)^{2+}$ | 427[a] | 432 | 5 | 614 | 606 | −8 | 20,550 | 2.06 | 970 | 1160 ± 30(1) |
| | | | | | | | | | | 5290 ± 80(2) |
| $Ru(DIP)_2(phen)^{2+}$ | 433 | 439 | 6 | 616 | 621 | −5 | 29,400 | 2.14 | 990 | 1160 ± 40(1) |
| | | | | | | | | | | 5100 ± 430(2) |
| $Ru(phi)_2(bpy)^{2+}$ | 572 | 582 | 10 | b | | | 75,300 | — | | — |
| $Ru(phen)_2(phi)^{2+}$ | 535 | 544 | 9 | b | | | 51,900 | — | | — |
| $Ru(bpy)_2(phi)^{2+}$ | 535 | 548 | 13 | b | | | 48,000 | — | | — |

[a]The double-humped charge transfer bands characteristic of ruthenium polypyridyl complexes are such that the higher energy band of $Ru(phen)_2(DIP)^{2+}$ and $Ru(DIP)_2(phen)^{2+}$ is the more intense and is therefore defined as the $\lambda_{max}$ of the complex.
[b]Nonemissive complexes. $Ru(bpy)_2(phi)^{2+}$ was previously reported[15] to luminesce at 620 nm, but in our hands this was found to be due to $Ru(bpy)_3^{2+}$ contamination.
[c]Extinction coefficient for $Ru(5-NO_2-phen)_3^{2+}$ was taken from reference 15.
[d](1) and (2) denote first and second components of emission lifetime decay.

For those complexes which luminesce, changes in luminescence on DNA binding are found. Increases in emission are apparent with DNA binding, and depending upon the mixed ligand complex examined, red shifts or blue shifts in the emission spectra are observed (vide infra). As was seen earlier for $Ru(phen)_3^{2+}$ and $Ru(DIP)_3^{2+}$, (29,30) the decay in emission from the excited ruthenium complex in the presence of DNA is best characterized by a biexponential, with one component having an emission lifetime characteristic of the free ruthenium species, and one longer lived component. For $Ru(phen)_3^{2+}$ and $Ru(DIP)_3^{2+}$, this long lived component was characterized extensively and found to correspond to emission from the intercalatively bound species, the emission lifetime for the surface bound species was found to be indistinguishable from the free form. We suggest that the two components may be assigned similarly for these mixed ligand complexes. Moreover the similarity in spectroscopic perturbations seen with the mixed ligand complexes on binding to DNA supports the notion that these complexes also bind to DNA in a similar fashion.

The emission spectra and decay traces therefore suggest that the mixed ligand complexes all bind to DNA throught the mixture of two binding modes: intercalation and surface binding. The emission enhancements provide some gauge of the extent of intercalation as well as binding affinity. After corrections for the differeing affinities of phen and DIP mixed ligand complexes, from these data it appears that the intercalative component is actually quite comparable among the series. Quantitation of the surface versus intercalative components could not be made, however.

Figure 9:
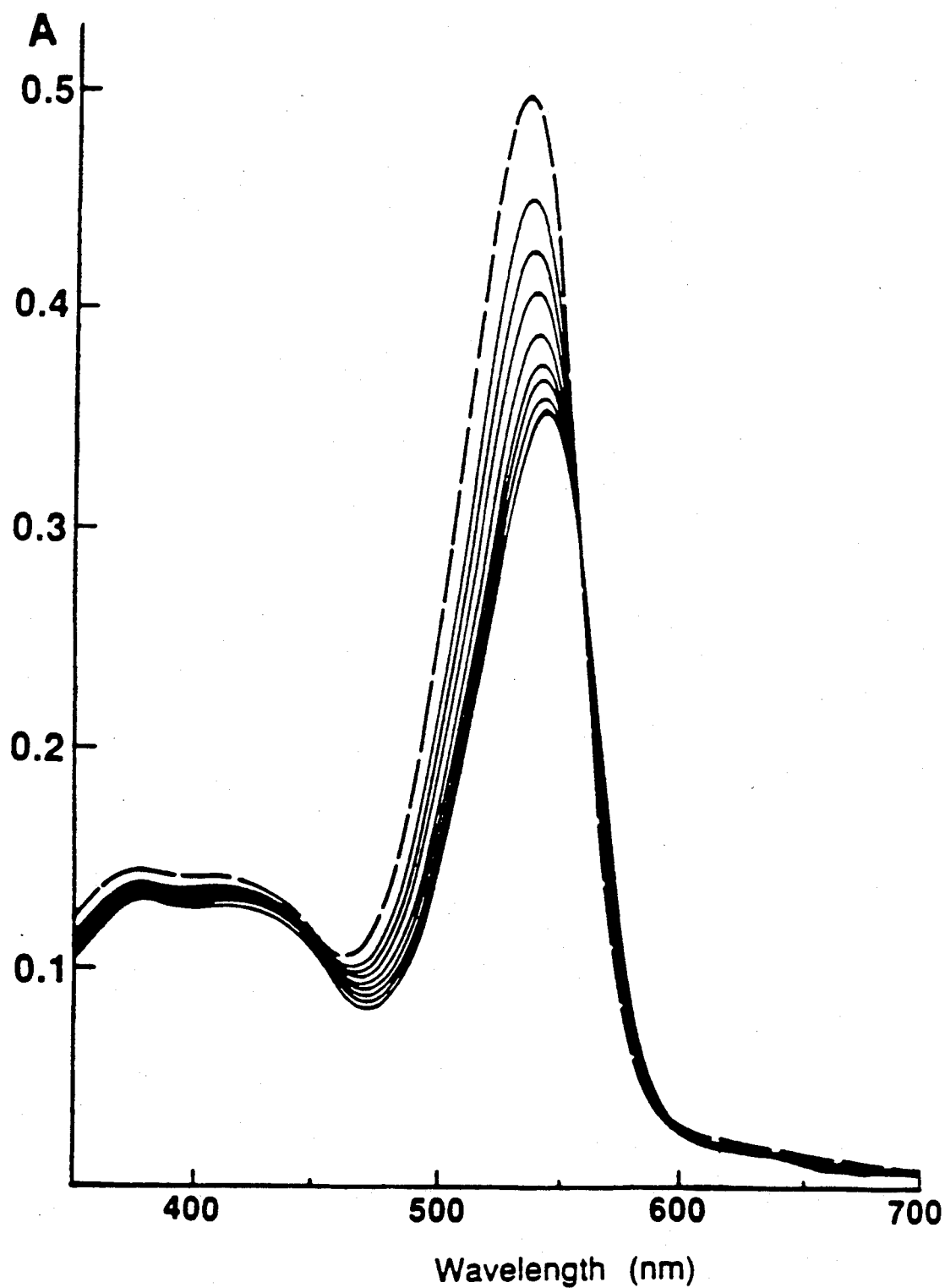
FIG. 9: Visible absorption spectra of $Ru(phen)_2(phi)^{2+}$ (10 μM) in the absence (---) and presence (-----) of increasing amounts of DNA (0.56 nucleotides/metal per scan).

The binding of intercalative drugs to DNA has also been characterized classically through absorption titrations, following the hypochromism and red shift associated with binding of the colored complex to the helix. (47) FIG. 9 displays a well-behaved titration of Ru(phen)$_2$(phi)$^{2+}$ with calf thymus DNA. Isosbestic points are observed at 558 nm and 598 nm. The spectra show clearly that addition of DNA yields hypochromism and a large red shift in the charge-transfer band of the complex. These spectral characteristics are attributable to a mode of binding which involves a strong stacking interaction between an aromatic chromophore and the base pairs of DNA.

The magnitudes of the red shift and hypochromism are furthermore commonly found to correlate with the strength of the interaction. (47) A comparison of red shifts found with DNA binding can be seen in Table 2. Complexes containing phi have the longest red shifts ($\leq 13$ nm), followed by DIP complexes ($\leq 6$ nm), phen complexes ($2 \leq$ nm), and bpy complexes (no red shift). Thus, if red shifts upon binding are taken as a measure of stacking interaction, a trend can be observed in which the optimal shape for intercalation is phi > DIP > phen > bpy.

Figure 10:
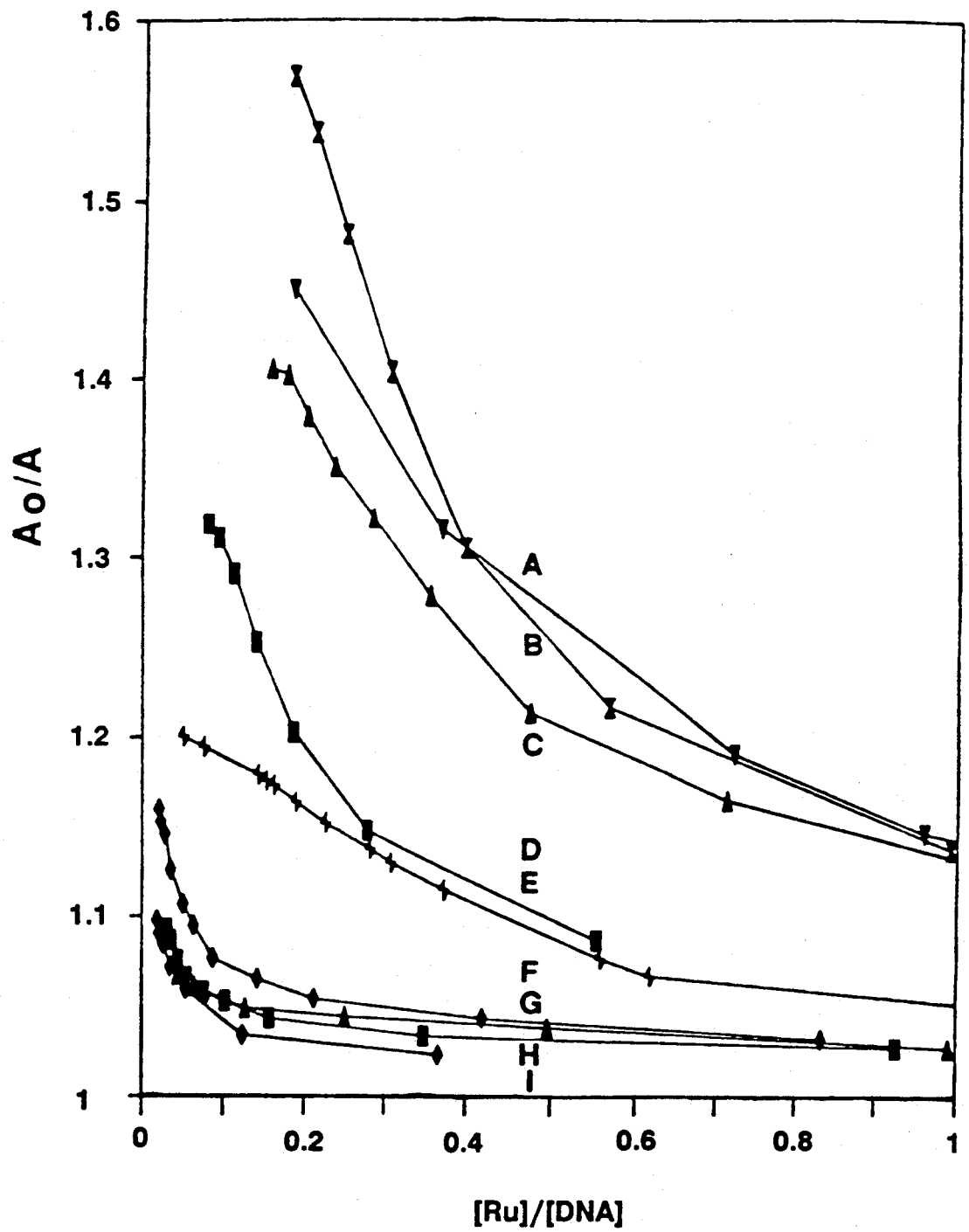
FIG. 10: Hypochromism in the visible charge transfer band as a function of [Ru]/[DNA]. Ao/A represents the ratio of absorbance of free ruthenium (in the absence of DNA) to the absorbance as a function of increasing concentrations of added DNA. $A=(Ru(DIP)_2(phen)^{2+}$, $B=Ru(phi)_2(bpy)^{2+}$, $C=Ru(phen)_2(phi)^{2+}$, $D=Ru(bpy)_2(phi)^{2+}$, $E=Ru(phen)_2((DIP)^{2+}$, $F=Ru(phen)_3^{2+}$, $G=Ru(5NO_2\text{-}phen)_3^{2+}$, $H\text{-}Ru(phen)_2(flone)^{2+}$, $I\text{-}Ru(phen)_2(bpy)^{2+}$.

The degree of hypochromism generally correlates well also with overall binding strength FIG. 10 shows absorption titration data for the series of complexes as a function of DNA addition. The extent of hypochromicity in the charge transfer band as a function of DNA binding, plotted reciprocally as $A_0/A$ versus [Ru][DNA], is found to provide a good measure of relative binding affinity, since the hypochromicity found for the series of complexes per DNA added parallels nicely the binding results by equilibrium dialysis. Ru(bpy)$_2$(phi)$^{2+}$, a soluble complex of high binding strength to DNA, and the more hydrophobic complexes Ru(phen)$_2$(DIP)$^{2+}$, Ru(DIP)$_2$(phen)$^{2+}$ and Ru(phi)$_2$(bpy)$^{2+}$ show the greatest change in absorption with DNA addition. The latter three complexes, however, are only sparingly soluble in the buffer solution and may show increased hypochromism owing to aggregation, both in solution and bound to the helix. Complexes which bind only weakly to DNA, such as Ru(bpy)$_3^{2+}$ and Ru(bpy)$_2$(phen)$^{2+}$, are seen to show little hypochromic effect.

Determinations of intrinsic binding constant, $K_b$, based upon these absorption titrations may be made using the following equation: (48)

$$[DNA]/(\epsilon_A-\epsilon_F)=[DNA]/(\epsilon_B-\epsilon_F)+1/K_b(\epsilon_B-\epsilon_F)$$

where $\epsilon_A$, $\epsilon_F$, and $\epsilon_B$ correspond to $A_{obs}/[Ru]$, the extinction coefficient for the free ruthenium complex, and the extinction coefficient for the ruthenium complex in the fully bound form, respectively. In plots of $[DNA]/(\epsilon_A-\epsilon_F)$ versus [DNA], $K_b$ is given by the ratio of the slope to intercept. This half-reciprocal absorption titration method, which has been used successfully to determine the intrinsic $K_b$ of molecules as hydrophobic as benzo[a]pyrene derivatives, (48) was found to provide a useful route to obtain intrinsic binding constants for the broad range of ruthenium complex of differing solubilities. Values for $K_b$, given in Table 1, were obtained for all but those complexes which bound very weakly, the compounds Ru(bpy)$_3^{2+}$, Ru(bpy)$_2$(phen)$^{2+}$, Ru(bpy)$_2$(DIP)$^{2+}$, Ru(5NO$_2$-phen)$_3$, and Ru(phen)$_2$(flone)$^{2+}$ showed such small changes in their absorption specta upon DNA addition, that the resultant error in $\epsilon_A-\epsilon_F$ was large. For the remainder, as shown in Table 1, good correlation with those values obtained by dialysis was found.

Figure 11:
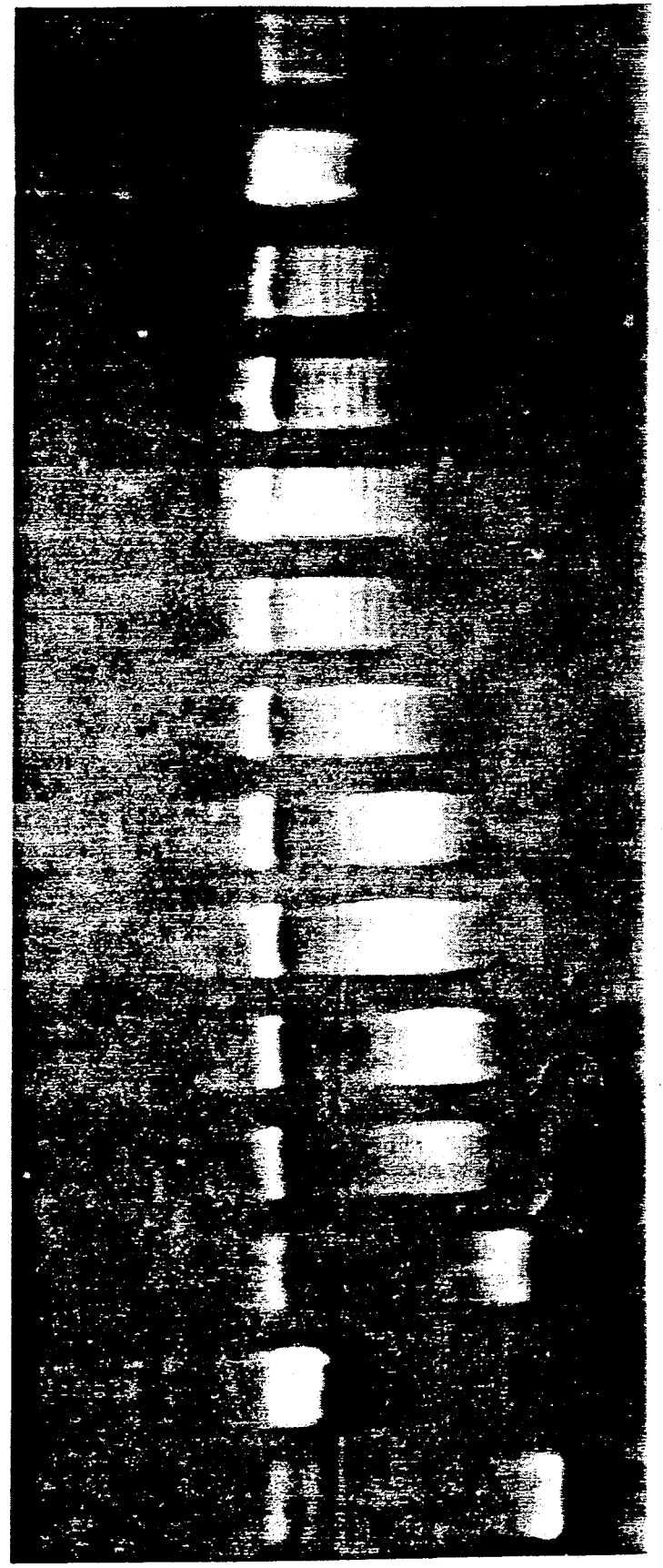
FIG. 11: Unwinding of pBR322 DNA by $Ru(bpy)_2(phi)^{2+}$ after incubation with topisomerase 1 in the presence of increasing concentrations of ruthenium complex as described in the Experimental Section. Lane 1 is DNA control, Lane 2 is DNA and topoisomerase alone, Lanes 3-14 are DNA, topoisomerase, and decreasing Ru concentrations from 5.74 μM to 1.57 μM. I and II denote forms I and II DNA.

Unwinding of Supercoiled DNA: The amount of helical unwinding induced by a complex bound to closed circular DNA provides another measure of intercalative binding. (48,49) Helix unwinding by a noncovalently bound species is determined by observing the change in superhelical density in a plasmid, after relaxation of the plasmid in the presence of bound complex by topoisomerase I and then removal of the complex. The helix unwinding angle is defined as the number of degrees of base pair unwinding per complex bound (see Experimental). FIG. 11 shows the change in superhelical density of pBR322 DNA dinner after incubation with increasing concentrations of Ru(bpy)$_2$(phi)$^{2+}$ in the presence of topoisomerase. Table 1 includes both the concentration of ruthenium complex added to unwind the plasmid 50% (11 out 22 superoils removed), and, for those complexes which show well behaved binding parameters, the corresponding unwinding angle per complex bound.

Several trends are apparent from these data. First, those complexes with appreciable binding affinity show reasonable values for the unwinding consistent with intercalation. Ru(phen)$_3^{2+}$ and Ru(phen)$_2$(phi)$^{2+}$ display unwinding angles of 19° (50) and 26°, respectively, and these may be compared to that of 26°, found for ethidium (43), a classical DNA intercalator. For the complexes which bind with lower overall binding strength, unwinding angles could not be reliably determined. The data indicate, however, the inverse correlation between binding constant and concentration of complex required for a constant amount of unwinding. Therefore it is likely that, for this series of weaker binding molecules, the unwinding angle per complex bound is quite similar. It is noteworthy that bound concentrations reflect both intercalation and surface binding and thus if surface binding contribute little to the unwinding, those complexes with a greater percentage in the surface bound form will show reduced apparent unwinding angles. Ru(bpy)$_3^{2+}$, which based upon spectroscopic results, neither intercalates nor surface-binds to the helix, shows little significant unwinding of the helix. The complexes Ru(DIP)$_2$(phen)$^{2+}$ and Ru(phi)$_2$(bpy)$^{2+}$ proved to be too insoluble for application of the unwinding assay. For the complexes possessing high binding affinity, a larger certainty in bound concentration and therefore unwinding angle exists. Here some effect of the ancillary ligand may be seen Ru(phen)$_2$(phi)$^{2+}$ exhibits a somewhat greater unwinding angle than Ru(bpy)$_2$(phi)$^{2+}$, suggesting that the larger ancillary phen ligands may contribute to unwinding of the helix.

Figure 12:
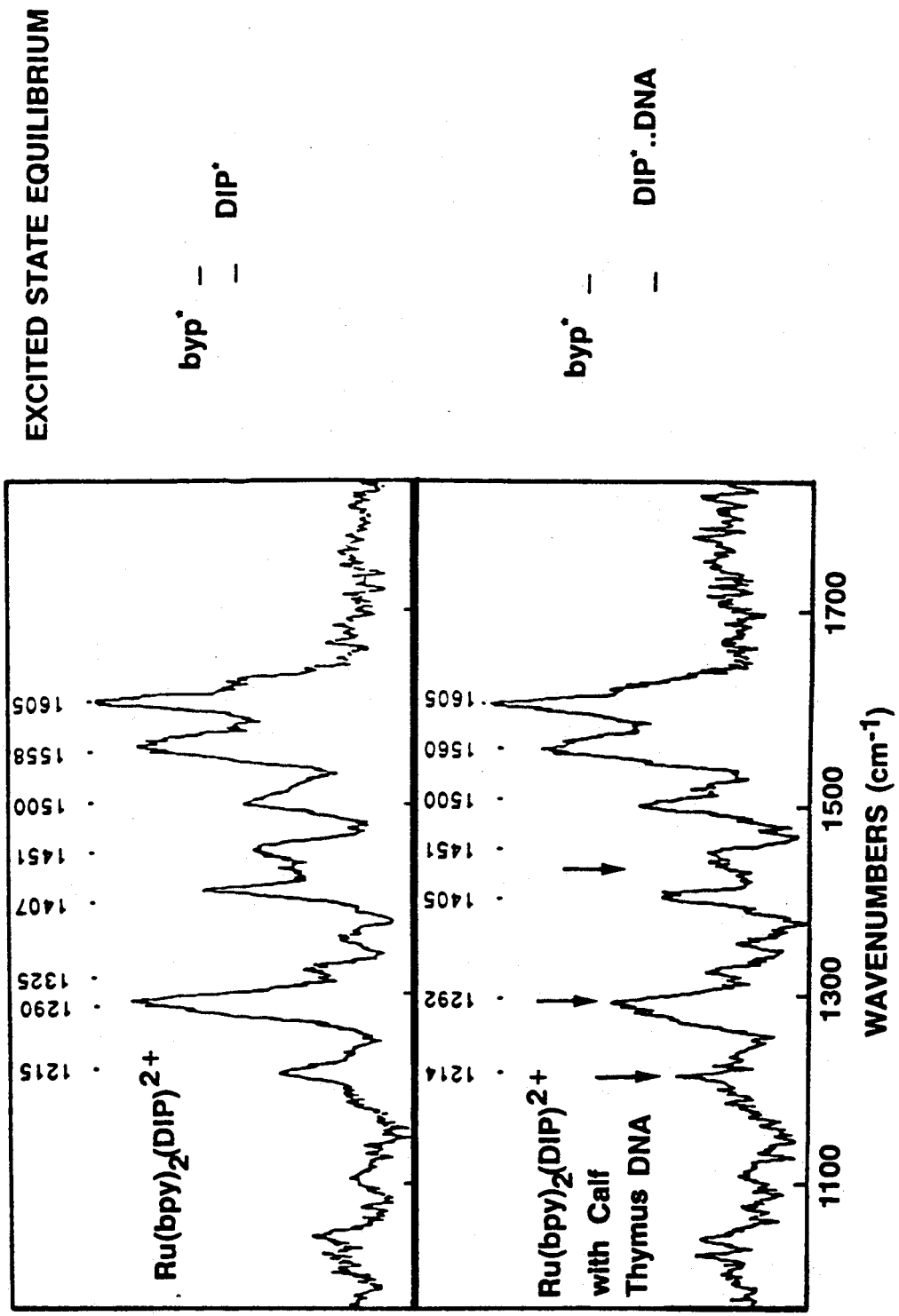
FIG. 12: Excited state resonace Raman spectrum of $Ru(bpy)_2DIP^{2+}$ in the absence (top) and presence (bottom) of calf thymus DNA. The arrows indicated those transitions determined earlier[30] to reflect excited state charge transfer which is localized onto the bypy ligand. These spectra indicate that in the presence of DNA the intensity of transitions dominated by charge localization onto bpy is reduced relative to those dominated by charge transfer to the DIP ligand.

Effects of DNA Binding seen by Excited State Resonance Roman Spectroscopy: The effects of DNA binding on the electronic structure of the complexes may also be probed by excited state resonance Raman spectroscopy, and this technique has provided some novel evidence in support of intercalative binding. FIG. 12 shows spectra for Ru(bpy)$_2$DIP$^{2+}$ in the absence and presence of DNA. In the spectra of mixed ligand complexes, transitions were assigned earlier to excited states localized either on bpy or DIP. (51) Thus, the presence of an equilibrium between the two localized excited states was established In particular the transitions centered at 1215 and 1290 cm$^{-1}$ are dominated by bpy*. This equlibrium can be shifted on binding to DNA. In the presence of DNA, the intensity of the transitions corresponding to bpy* are considerably decreased relative to those for DIP*. Remarkably, though not covalently bound, the association with DNA sufficiently perturbs the excited state electronic structure of the complex for detection by this technique We interpret this decrease in bpy* transitions relative to DIP* to reflect the shift in excited state equilibrium toward DIP*. For this mixed ligand complex, only the DIP ligand, rather than bpy, is expected to intercalate into the helix. Perhaps as a result of binding to DNA, the energy of DIP* is lowered more so than is bpy*, with charge transfer occurring preferentially onto the intercalated DIP ligand.

One may also understand the red and blue shifts in emission associated with binding to DNA by the mixed ligand complexes by considering these shifts in equilibria. For Ru(bpy)$_2$DIP$^{2+}$, the lower energy excited state involves transfer to the DIP ligand. (51) If DIP is the intercalating ligand, this state is lowered in energy, and, consistent with this idea, a red shift (10 nm) in emission is observed. In the case of Ru(bpy)$_2$phen$^{2+}$, the lower energy excited state involves charge transfer onto the bpy ligand. (51) Since the phen ligand is the one which would intercalate and thus be lowered in energy, an overall blue shift of 9 nm is observed. The same arguments may explain the shifts observed for Ru(phen)$_2$bpy$^{2+}$ and Ru(DIP)$_2$phen$^{2+}$. For Ru(phen)$_2$DIP$^{2+}$ the direction of the shift found is unexpected, but this may reflect underlying contributions from surface binding

Discussion

The result fo these varied experiments on the series of mixed ligand complexes of ruthenium(II), when taken together, provide a detailed picture of factors affecting noncovalent binding of the complexes to the helix. The complexes, excepting Ru(bpy)$_3^{2+}$, all appear to intercalate and surface-binding into DNA. This conclusion is based upon the effects of hypochromism, the increases in emission intensities and excited state lifetimes, the helical unwinding, and the excited state resonance Raman experiment. (52) The chiral discrimination found in binding these complexes to DNA lends further support to the intercalative binding model and more specifically to the notion that the binding of this family of rigid complexes with respect to the helix is likely to be quite similar. (53) In this series of mixed ligand complexes, we have varied geometry, hydrophobicity, size, dipole moments, and hydrogen bonding ability, and we may therefore examine how each of these factors contribute to DNA binding.

Intercalation and Surface Binding: For the mixed ligand complexes, the tendencies of each of the ligands to intercalate may be compared. For the series RuX$_2$bpy$^{2+}$, RuX$_2$phen$^{2+}$, RuX$_2$DIP$^{2+}$, RuX$_2$phi$^{2+}$, where the ancillary, non-intercalated ligands, X, are kept constant, the binding constants increase in the series bpy<<phen≦DIP<<phi. This variation likely reflects the differing ability of the ligands to stack and overlap well with the base pairs. The phi ligand is flat, large in surface area, and has a geometry which permits substantial overlap with the base pairs (rather than one where the majority of the $\pi$ orbital framework would lie in the center of the helix, between the DNA bases) Hence the phi ligand is well suited for intercalation, and for mixed ligand complexes it would be the phi ligand which would be expected preferentially to intercalate. The DIP ligand, similar in expanse to that of phi, is not expected to be flat, with phenyl groups instead twisted out of the phenanthroline plane, (54) and this lack of planarity diminishes the favorability of the ligand for intercalation. Nonetheless, the data are consistent with intercalation by this ligand. The DIP ligand, moreover, may be favored over phen for intercalation into the helix. Binding data from absorption titrations for Ru(phen)$_3^{2+}$ and Ru(phen)$_2$DIP$^{2+}$ show increased binding affinity upon substitution with DIP, and both emission enhancements and red shifts in absorption are greater for analogous DIP versus phen complexes. That this affinity derives from intercalation rather than from added hydrophobic surface binding is not definitively estalbished, however, and therefore the relative intercalative ability of DIP versus phen complexes is difficult to assess. The phen ligand can, nonetheless, also intercalate into the helix, though the ancillary ligands preclude substantial overlap with the base pairs Inspection of models shows that, owing to the overhanging hydroggen atoms (2 and 3 positions) from the ancillary ligands, only the outer third of the phenanthroline ligand (5 and 6 positions) s available for stacking. Thus only a partial insertion of the ligand is likely. For bpy, this stacking region is absent. On this basis, it is reasonable to understand why the bpy ligand shows only an electrostatic association with DNA, and no detectable intercalation.

Effects of Ancillary Ligands: The primary effect of the ancillary ligand is in altering the extent of enantioselectivity. As was found earlier (29) in comparisons of Ru(phen)$_3^{2+}$ and Ru(DIP)$_3^{2+}$, increased asteric bulk of the ancillary ligand increases the enantioselectivity for intercalation of the Δ isomer into right-handed DNA. Given intercalation into the helix by one ligand, we can also compare how different ancillary ligands add to or detract from the overall binding affinity. One bulky hydrophobic ligand which can intercalate ads to the stability of the bound complex, but the second bulky ligand, which would necessarily ocupy the ancillary position, perpendicular to the groove, adds no further stability. Ru(DIP)$_2$phen$^{2+}$ shows binding similar to that of Ru(phen)$_2$DIP$^{2+}$, and Ru(phi)$_2$bpy$^{2+}$ actually displays decreased affinity for DNA relative to Ru(bpy)$_2$phi$^{2+}$. For these ancillary ligands, steric interactions may interfere with how deeply the intercalated ligand may stack into the helix. Additionally, the increased hydrophobicity of the complexes leads to selfstacking in solution, and this effect may reduce the net binding affinity. (55) Interestingly, symmetric substitutions provide a different picture. In comparing Ru(bpy)$_2$phen$^{2+}$ with Ru(phen)$_3^{2+}$, or Ru(bpy)$_2$DIP$^{2+}$ with Ru(phen)$_2$DIP$^{2+}$, one finds increased DNA binding affinity with increasing hydrophobicity of the ancillary ligands. (56) This observation may in part reflect a greater tendency of phen for surface binding. However the orientations of the intercalated complexes will certainly affect their ability to exclude water from the hydrophobic surfaces of the ancillary ligands, and this may be particularly important in stabilizing symmetric binding molecules.

Hydrogen Bonding: The series of complexes studied also afford the opportunity to examine whether substitutions of ligands which contain potentially hydrogen bonding groups stabilize the complexes bound to DNA.

Both the red shift in absorption titrations and the finding of enantioselective binding of the Δ isomer suggest that Ru(5-NO$_2$-phen)$_3{}^{2+}$ may bind to DNA intercalatively. One might have expected that with the larger heterocyclic surface of 5-NO$_2$-phen, the ligand might even have been favored for intercalation. Inspection of models suggests that if intercalated, or indeed even if surfacebound, the nitro-groups on the ancillary ligands could be aligned appropriately for hydrogen bonding to base positions. The complex, however, binds only poorly to DNA. In fact the binding constant is comparable to that of Ru(bpy)$_3{}^{2+}$ and thus the major source of stabilization is likely to be electrostatic. A similar conclusion may be drawn based upon a comparison of binding constants of Ru(phen)$_2$bpy$^{2+}$ and Ru(phen)$_2$flone$^{2+}$. For the diazafluoreneone ligand, the oxygen atom is oriented perpendicular to the main axis of phenanthroline and thus the orientation of the hydrogen bonding acceptor relative to that of either groove containing hydrogen bonding donors differs from that in Ru(5-NO$_2$-phen)$_3{}^{2+}$. Yet, again, no increased stabilization is detected. Instead the binding affinity for Ru(phen)$_2$flone$^{2+}$ is indistinguishable from that for Ru(phen)$_2$bpy$^{2+}$. It appears, then, that the substitution of potential hydrogen bonding acceptors onto the phenanthroline ligands provides no additional source of stabilization. The same observation applies to our single example of a hydrogen bonding donor on an ancillary ligand, Ru(phi)$_2$bpy$^{2+}$. For this complex, equilibrium binding constants are in the range of those for Ru(phen)$_2$phi$^{2+}$.

Thus, although specific hydrogen bonding interactions along the DNA helix are possible, there is apparently no net increase bonding stabilization relative to that where the DNA and complex are independently solvated. In binding to DNA, some new hydrogen bonds between DNA and complex may be made, but these are at the expense of hydrogen bonds for each with solvent.

Overall Factors Contributing to Stabilization: If one compares the various factors that contribute to stabilizing the metal complexes on the DNA helix, it appears that the most significant factor is that of molecular shape. Those complexes which fit most closely against the DNA helical structure, those in which Van der Waals interactions between complex and DNA are maximized, display highest binding affinity. The phi ligand, for example, is constructed to provide substantial overlap of its aromatic surface with that of the DNA base pairs, and binding constants for those complexes with phi as intercalated ligand show more than two orders of magnitude increase in binding affinity. The phi ligand is not well suited as an ancillary ligand, and fact more stability results from ancillary substitution by DIP rather than by phi. This notion is further exemplified in the differences between symmetrically and non-symmetrically arranged ancillary ligands, or even more simply in comparisons of binding modes and affinities for phen versus bpy complexes.

Table 3 summarizes two characteristics of the complexes which may be useful to consider: their solubility in buffer and their water accessible surface areas. (57) Some correlations between these parameters and the intrinsic binding constants of the complexes may be made, and also some deviations are apparent. Certainly the hydrophobicity of a complex appears to be an important criterion in determining binding affinity. Those complexes with more surface area for interaction with DNA and for which interactions with DNA rather than with water are favored display higher overall intrinsic binding constants. Hydrogen bonding funtionalities do not appear to be critical to overall binding stability. Indeed, Ru(5-NO$_2$-phen)$_3{}^{2+}$ and Ru(phen)$^2{}_2$flone show binding affinities much lower than would be expected based upon their solvent accessible surfaces. Since binding to DNA limits hydrogen bonding interactions of the free complex with water, the overall free energy change in binding to DNA is reduced by this factor. In contrast, the free energy change in binding to DNA is increased for hydrophobic complexes because of the entropy gain associated with release of water molecules solvating the hydrophobic ligands. Binding affinities for the DIP complexes are, however, not as high as would be expected based upon calculations of accessible surface area, and this is likely because the ligand is not planar. Hydrophobicity is an important factor, but the shape of the complex, the disposition of ligands relative to the helix and how the ligands fit against the DNA surface, appears to be critical for both intercalative and surface-bound interactions.

TABLE 3

Characteristics of Complexes

| Complex | Solubilities in Buffer$^a$ (mM) | Water-Accessible Surface Area$^b$ (Å$^2$) |
|---|---|---|
| Ru(bpy)$_3{}^{2+}$ | 94. (4.4) | 687.3 |
| Ru(bpy)$_2$(phen)$^{2+}$ | 200. (24.) | 702.6 |
| Ru(phen)$_2$(bpy)$^{2+}$ | 133. (1.8) | 719.6 |
| Ru(phen)$_3{}^{2+}$ | 159. (5.3) | 736.7 |
| Ru(5-NO$_2$phen)$_3{}^{2+}$ | 28.2 (.27) | 862.6 |
| Ru(phen)$_2$(flone)$^{2+}$ | 60. (2.2) | 738.9 |
| Ru(bpy)$_2$(DIP)$^{2+}$ | 73. (2.5) | 916.4 |
| Ru(phen)$_2$(DIP)$^{2+}$ | 9. (1.2) | 950.2 |
| Ru(DIP)$_2$(phen)$^{2+}$ | 0.18 (.01) | 1166.7 |
| Ru(bpy)$_2$(phi)$^{2+}$ | 15. (2.0) | 768.3 |
| Ru(phen)$_2$(phi)$^{2+}$ | 0.17 (.01) | 809.4 |
| Ru(phi)$_2$(bpy)$^{2+}$ | 0.018 (.001) | 854.0 |

$^a$Measured from saturated solutions in 5 mM Tris, 50 mM NaCl, pH 7.5 after 24 hrs., 25 C. Solubilities are given for the chloride salts. Standard deviations are given in parentheses.
$^b$See reference 36.

Shape and hydrophobicity are likely to be important factors governing also the ability of other small molecules to bind to DNA, as well. It must be noted, however, that these studies do not directly provide insight into those factors which may govern differential DNA site-selectivity. Site-specific DNA cleavage studies using analogous mixed ligand complexes of rhodium (III) are in progress to address that issue. (58)

Utility of Transition Metal Complexes: Coordination chemistry could play a unique role in the development of new compounds which bind site-specifically to biopolymers. Given the structural flexibility and variable dimensionality of transition metal complexes, one may design and readily prepare a different repertoire of shapes for interaction with DNA than those obtained through organic synthesis alone. Mixed ligand complexes of ruthenium(II) are particularly well suited to these systematic investigations of recognitition. The octahedral transition metal ion provides the core, in fact a chiral center, for a rigid well defined structure of coordinated ligands. The ligands may be varied in a synthetically convenient fashion to produce a family of substitutionally inert DNA binding molecules, with a range of ligand functionalities. The intense coloration and rich excited state properties of the complexes provide a sensitive spectroscopic handle to monitor binding interactions. These and similar complexes may therefore be useful also in studies of recognition of other biopolymers.

References

1. Sutin. N; Creutz. C.. Pure Appl. Chem.. 1980. 52, 2717.
2. Kalyasundaram. K., Coord. Chem. Rev., 1982. 46, 159.
3. Meyer, T. J.. Pure Appl. Chem.. 1986. 58, 1193.
4. Ghosh. P. K; Bard, A. J., J. Phys. Chem., 1984. 88, 5519. Krenske. D..; Abto. S.; Van Damme. H.; Cruz, M.; Fripiat. J. J., J. Phys. Chem., 1980. 84. 2447.
5. Kumar, C. V.; Barton, J. K.; Turro. N. J., J. Am. Soc., 1985, 107, 5518. Barton, J. K., Science (Washington D.C.) 1986. 233. 727.
6. Juris A.; Barigelletti. F.; Balzani, V.; Belser, P.; von Zelewsky, A., Isr. J. Chem. 1982, 22,87.
7. Belser, P.; von Zelewsky, A.; Zehnder, M., Inorg. Chem., 1981, 20, 3098.
8. Warren, L. Inorg. Chem.. 1977, 16, 2814.
9. Tom Dieck. H.; Reick. I., Angew. Chem., int. Ed. Engl. 1970, 9, 793.
10. Schlosser, v. K. Z., Chem.. 1970, 10,439.
11. Tuchtenhagen, G.; Ruhlmann, K.. Justus Liebigs Ann. Chem., 1968. 711. 174.
12. Schlosser, v. K. Z., Anorg. Allg. Chem.. 1972. 387, 91.
13. Blue ruthenium species are produced in great quantity if the reaction is allowed to reflux too long or if concentrated solutions of Ru(phi)$_3^{2+}$ are allowed to stand for long periods of time. Chromatography has shown these species to be variable and high in molecular weight. Deep blue ruthenium species have been observed previously and formulated either as clusters or ligand-bridged multinuclear species.[14]
14. Rose. D.; Wilkinson, G., J. Chem. Soc. A. 1970. 1791.
15. Curtis. J.; Sullivan. B. P.; Meyer. T. J., Inorg. Chem., 1983. 22, 224.
16. Gutmann. V.. The Donor-Acceptor Approach to Molecular Interactions. Plenum: New York, 1978.
17. The additional intense band at 510 nm leads to the purple coloration in the complex. A comparable pair of low-energy transitions are found in the benzoquinone dimine derivative. ®
18. Ackerman, M. N.; Interrante, L. V., Inorg. Chem., 1984, 23, 3904.
19. Mabrouk. P. A.; Wrighton. M. S., Inorg. Chem., 1986, 25, 526. Dumar, C. V.; Gould, I. S.; Barton, J. K.; Turro, N. J., submitted for publication.
20. It is interesting that the transition centered at 510 nm in Ru(phi)$_3^{2+}$ is not at all apparent in mixed-ligand complexes containing the phi ligand. Instead, the 525-nm transition in Ru(bpy)$_2$(phi)$^{2+}$ species. The visible spectrum of Ru(bpy)(phi)$_2^{2+}$ (data not shown) shows visible transitions centered at 472 and 572 nm, consistent with some degree of delocalization.
21. A similar delocalization may explain the intense visible transition in the ruthenium cage complex recently prepared by Sargeson, et al. (personal communication).
22. Barton, J. K., Science 1986, 233, 727.
23. Dervan, P. B., Science 1986, 232,464; Wade, W. S.; Dervan, P. B. J. Am. Chem. Soc. 1987 109, 1574.
24. Berman, H. M.; Young, P. R. Ann. Rev. Biophys. Bioeng. 1981 10, 87.
25. Waring, M. J.; Fox, K. R.; Grigg, G. W. Biochem. J. 1987 143, 847; Burckhardt, G.; Waehnert, U.; Luck, G.; Zimmer, C. Stud. Biophys. 1986 114, 225; Kissinger, K. Krowicki, K., Dabrowiak, J. C., Lown, J. W. Biochemistry 1987 26, 5590.
26. Quigley, G. J.; Ughetto, G.; van der Marel. G.; van Boom. J. H.; Wang, A. H.-J.; Rich. A. Science 1986 232, 1255; Kopka, M. L.; Yoon, C.; Goodsell. D.; Pjura, P.; Dickerson, R. E. Proc. Natl. Acad. Sci. U.S.A. 1985 82, 1376; Pjura, P. W.; Grezeskowiak, K.; Dickerson, R. E. J. Mol. Biol 1987 197, 257.
27. Wilson, W. D.; Wang, Y-H.; Kusuma, S.; Chandrasekaran, S.; Yang. N. C.; Boykin, D. W. J.Am. Chem. Soc. 1985, 107, 4989-4995.
28. Breslauer, K. J.; Remata, D. P.; Chou, W. Y.; Ferrante, R.; Curry, J.; Zaunczkowski, D.; Snyder, J. G.; Marky, L. A. Proc. Natl. Acad. Sci. U.S.A. 1987 84, 8922; Ibanez, V.; Geacintov, N. E.; Gagliano, A. G.; Brondimarte, S.; Harvey, R. G. J. Am. Chem. Soc. 1980, 102, 5661.
29. Kumar, C. V.; Barton, J. K.; Turro, N. J. J. Am. Chem. Soc. 1985, 107, 5518.
30. Barton, J. K.; Goldberg, J. M.; Kumar, C. V.; Turro, N. J. J. Am. Chem. Soc. 1986. 108, 2081; J. Rehmann, Ph.D. Dissertation. Columbia University.
31. Mei, H.-Y.; Barton, J. K. Proc. Natl. Acad. Sci. U.S.A. 1988, 85, 1339; Barton J. K.; Raphael, A. L. Proc. Natl. Acad. Sci. U.S.A. 1985, 82, 6460.
32. Kirshenbaum, M. R.; Tribolet, R.; Barton, J. K. Nucl. Acids Res. 1988. 16, 7943.
33. Meyer, T. J. Pure and Appl. Chem. 1986 58, 1193; Sutin. N. and Creutz, C. Pure and Appl. Chem. 1980 52, 2717.
34. Belser, P.; von Zelewsky, A. Zehnder, M. Inorg. Chem. 1981 20, 3098.
35. Pyle, A. M.; Barton, J. K. Inorg. Chem. 1987 26, 3820.
36. Krause, R. A. Inorg. Chim. Acta 1977 22, 209.
37. Lin, C.-T.; Botcher, W.; Chou, M.; Creutz, C.; Sutin, N. J. Am. Chem. Soc. 1976 98, 6536.
38. Henderson, L. J.; Fronczek, F. R.; Cherry, W. R. J. Am. Chem. Soc. 1984 106, 5876.
39. Mass spectral data are reported as mass/ion values, rather than mass/charge ratios.
40. Kumar, C. V.; Barton, J. K.; Turro, N. J. Inorg. Chem. 1987 26, 1455.
41. Dallinger, R. F.; Woodruff, W. H. J. am. Chem. Soc. 1979 101 4391; Bradley, P. G.; Kress, N.; Hornberger, B. A.; Dallinger, R.; Woodruff, W. H. J. Am. Chem. Soc. 1981 103 7441. Smothers, W. K.; Wrighton, M. S. J. Am. Chem. Soc. 1983 105, 1067.
42. Keller, W. Proc. Natl. Acad. Sci. U.S.A. 1975 72, 4876.
43. Wang, J. C. J. Mol. Biol. 1974 89, 783.
44. Scatchard, G. Ann. NY. Acad. Sci 1949 51, 660.
45. McGheem J. D.; von Hippel, P. H. J. Mol. Biol. 1974 86, 469.
46. Mason, S. F.; Peart, B. J. J. Chem. Soc. Dalton Trans. 1973, 949.
47. Bloomfield, V. A.; Crothers, D. M.; Tinoco, Jr., I. Physical Chemistry of Nucleic Acids, Harper and Row, New York 1974, p. 432.
48. Wolfe, A.; Shimer, G. H.; Meehan, T. Biochem. 1987 26, 6392.
49. Waring, M. J. J. Mol. Biol. 1970 54, 247.
50. The unwinding angle for Ru(phen)$_3^{2+}$ has been measured by others as well and compares favorably with our determination. See Kelly, J. M.; Tossi, A.

B.; McConell, D. J.; OhVigin, C. Nucl. Acids. Res. 1985 13, 6017.
51. Kumar, C. V.; Barton, J. K.; Gould, I. R.; Turro, N. J.; Van Hooten. J. Inorg. Chem. 1988, 27, 648.
52. These results taken together provide strong evidence in support of intercalation, but only a crystal structure of the complex bound to the oligonucleotide may be considered definitive.
53. Although much can be inferred about the binding mode of the complex from these spectroscopic results, no conclusions may be drawn concerning similarities in where the complexes bind on the helix, either with respect to sequence to groove location.
54. Goldstein, B. M.; Barton, J. K.; Berman, H. M. Inorg. Chem. 1986 25, 842.
55. The fact that a lower concentration of $Ru(phi)_2$-$bpy^{2+}$ is needed for 50% helix unwinding compared to $Ru(bpy)_2phi^{2+}$ be consistent with this idea.
56. Consistent with this idea, both $Ru(DIP)_3^{2+}$ appear to bind DNA more avidly than their mixed ligand analogues, though their poor solubility makes the quantitative comparison difficult.
57. The calculations of solvent accessible surface area were performed using water as the probe molecule (radius of 1.58 A) using the program Macromodel, written by W. C. Still, Columbia University.
58. A. M. Pyle and J. K. Barton, unpublished results.

What is claimed:

1. A coordination complex of salt thereof which is spectroscopically or photoactively determinable when bound to DNA having the formula $$R_1-M-R_3 \quad \text{with } R_2 \text{ above } M$$

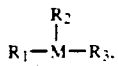

wherein M is Ru, Rh, Co, Fe, Cr, Cu, Zn, Cd, or Pb, and each of $R_1$, $R_2$, and $R_3$ is ethylenediamine, bipyridine, 2,2'-bipyridine (bpy), 4,4' diphenyl bipyridine, bis 4,4' methyl bipyridylate, bis 4,4' bipyridylamide, phenanthroline, 1,10-phenanthroline (phen), 4,7-diamino-1,10-phenanthroline, 3,8-diamino-1,10-phenanthroline, 4,7-diethylenediamine-1,10-phenanthroline, 3,8-diethylenediamine-1,10-phenanthroline, 4,7-dihydroxyl-1,10-phenanthroline, 3,8-dihydroxyl-1,10-phenanthroline, 4,7-dinitro-1,10-phenanthroline, 3,8-dinitro-1,10-phenanthroline, 4,7-diphenyl-1,10-phenanthroline (DIP), 3,8-diphenyl-1,10-phenanthroline, 4,7-dispermine-1,10-phenanthroline, 3,8-dispermine-1,10-phenanthroline, 5-nitro-phenanthroline, (5-$NO_2$phen), 3,4,7,8-tetramethyl-phenanthroline (TMP), diazafluorene-9-one, 4,5-diazafluorene-9-one (flone), phenanthrenequinonediimine, or 9,10-phenanthrenequinonediimine (phi); wherein $R_1$, $R_2$, and $R_3$ are bound to M by coordination bonds and wherein $R_1$ and $R_2$ are the same or different and both are different from $R_3$.

2. A complex of claim 1, wherein M is Ru, Rh, or Co.
3. A complex of claim 1, wherein $R_1$ and $R_2$ are the same.
4. A complex of claim 3 having the formula $M(phen)_2(phi)$, $M(bpy)_2(phi)$, $M(phi)_2(bpy)$, $M(phi)_2(4,4'\text{ diphenyl bipyridine})$, $M(\text{bis 4,4' methyl bipyridylate})_2(phi)$, $M(\text{bis 4,4' bipyridylamide})_2(phi)$, $M(bpy)_2(phen)$, $M(phen)_2(bpy)$, $M(phen)_2(flone)$, $M(bpy)_2(DIP)$, $M(phen)_2(DIP)$, or $M(DIP)_2(phen)$.
5. A complex of claim 4, wherein M is Ru, Rh, or Co.
6. A complex of claim 5, wherein M is Ru.
7. A complex of claim 5, wherein M is Rh.
8. A complex of claim 1 having the formula $M(\text{ethylenediamine})_2(phi)$ wherein M is Ru, Rh, or Co.
9. A complex of claim 5 having the formula $Ru(bpy)_2(phen)^{2+}$.
10. A complex of claim 5 having the formula $Ru(phen)_2(bpy)^{2+}$.
11. A complex of claim 5 having the formula $Ru(phen)_2(flone)^{2+}$.
12. A complex of claim 5 having the formula $Ru(bpy)_2(DIP)^{2+}$.
13. A complex of claim 5 having the formula $Ru(phen)_2(DIP)^{2+}$.
14. A complex of claim 5 having the formula $Ru(DIP)_2(phen)^{2+}$.
15. A complex of claim 5 having the formula $Ru(phi)_2(bpy)^{2+}$.
16. A complex of claim 5 having the formula $Ru(phen)_2(phi)^{2+}$.
17. A complex of claim 5 having the formula $Ru(bpy)_2(phi)^{2+}$.
18. A complex of claim 5 having the formula $Rh(phi)_2(bpy)^{3+}$.
19. A complex of claim 5 having the formula $Rh(phen)_2(phi)^{3+}$.
20. A complex of claim 7 having the formula $Rh(phi)_2(4,4'\text{ diphenyl bipyridine})^{3+}$.
21. A complex of claim 7 having the formula $Rh(\text{bis 4,4' methyl bipyridylate})_2(phi)^{3+}$.
22. A complex of claim 7 having the formula $Rh(\text{bis 4,4' bipyridylamide})_2(phi)^{3+}$.
23. A coordination complex or salt thereof which is spectroscopically or photoactively determinable when bound to DNA having the formula

wherein M is Ru or Rh and R is 9,10-phenanthrenequinone diimine or 5-nitrophenanthroline.

24. The optically resolved delta isomer of the complex of claim 1, 5, 8 or 23.
25. The optically resolved lambda isomer of the complex of claim 1, 5, 8 or 23.

* * * * *